United States Patent
Zhang et al.

(10) Patent No.: US 6,369,056 B1
(45) Date of Patent: Apr. 9, 2002

(54) CYCLIC UREA AND CYCLIC AMIDE DERIVATIVES

(75) Inventors: Puwen Zhang, Audubon; Arthur A. Santilli, Havertown; Andrew Fensome, Wayne; Eugene A. Terefenko, Quakertown; Andrew Q. Viet, Upper Darby, all of PA (US); Jay E. Wrobel, Lawrenceville, NJ (US); James P. Edwards, San Diego, CA (US); Todd K. Jones, Solana Beach, CA (US); Christopher M. Tegley, Thousands Oaks, CA (US); Lin Zhi, San Diego, CA (US)

(73) Assignees: American Home Products Corporation, Madison, NJ (US); Ligand Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/552,356

(22) Filed: Apr. 19, 2000

Related U.S. Application Data

(60) Provisional application No. 60/183,037, filed on May 4, 1999.

(51) Int. Cl.$^7$ .................. A61K 31/535; C07D 273/00; C07D 265/00; C07D 265/12
(52) U.S. Cl. ................ 514/230.5; 544/70; 544/71; 544/92
(58) Field of Search .................. 514/230.5; 544/70, 544/71, 92

(56) References Cited

U.S. PATENT DOCUMENTS

| | | | | |
|---|---|---|---|---|
| 3,635,964 A | 1/1972 | Skorcz et al. | ............ | 260/247.1 |
| 3,917,592 A | 11/1975 | Kobzina | ................. | 260/244 |
| 4,093,730 A | 6/1978 | Butti | .......................... | 424/270 |
| 4,440,785 A | 4/1984 | Walsh | ......................... | 424/317 |
| 4,666,913 A | 5/1987 | Kubla et al. | ................. | 514/259 |
| 4,670,566 A | 6/1987 | Walsh | ......................... | 548/485 |
| 4,721,721 A | 1/1988 | Kuhla | ......................... | 514/312 |
| 4,822,794 A | * 4/1989 | Spada et al. | ............. | 514/230.5 |
| 4,831,027 A | 5/1989 | Narr et al. | ................... | 514/212 |
| 4,853,473 A | 8/1989 | Fischer et al. | ............. | 549/326 |

(List continued on next page.)

FOREIGN PATENT DOCUMENTS

| | | |
|---|---|---|
| DE | 3633861 | 4/1988 |
| DE | 43 30 234 | 3/1995 |
| DE | 43 44 463 | 6/1995 |
| EP | 022317 | 1/1981 |
| EP | 0 208 510 | 1/1987 |
| EP | 311135 | 4/1989 |
| EP | 385850 | 9/1990 |
| EP | 483077 | 9/1991 |
| EP | 454330 | 10/1991 |
| EP | 0 535 529 | 9/1992 |

(List continued on next page.)

OTHER PUBLICATIONS

K. Horowitz et al., "Progestin, Progesterone Receptors, and Breast Cancer", "Hormones and Cancer", publisher: Birkhaeuser, Boston, Mass., ed. Vedeckis, p. 283–306 (1996).

Mamaev, V.P., et al., "Synthesis of 4H–Thieno [3,2–B] Pyrrol–5(6H)–One" Bulletin of the Academy of Sciences on the USSR. Division of Chemical Science, US, Consultants Bureau. New York. vol. 9, p. 1549–1553, 1966.

(List continued on next page.)

*Primary Examiner*—Richard L. Raymond
*Assistant Examiner*—Tamthom N. Truong
(74) *Attorney, Agent, or Firm*—Howson and Howson

(57) ABSTRACT

This invention provides compounds of the formula:

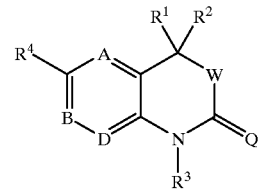

wherein: A, B and D are N or CH, with the proviso that A, B and D can not all be CH; $R^1$ and $R^2$ are independent substituents selected from H, $COR^A$, $NR^B COR^A$, or optionally substituted alkyl, alkenyl, alkynyl, cycloalkyl, aryl, or groups; or $R^1$ and $R^2$ are fused to form an optionally substituted 3 to 8 membered spirocyclic or heterocyclic ring; $R^A$ is H or optionally substituted alkyl, aryl, alkoxy, or aminoalkyl; $R^B$ is H, $C_1$ to $C_3$ alkyl, or substituted $C_1$ to $C_3$ alkyl; $R^3$ is H, OH, $NH_2$, or optionally substituted alkyl, or alkenyl, or $COR^C$; $R^C$ is H or optionally substituted alkyl, aryl, alkoxy, or aminoalkyl; $R^4$ is a substituted benzene ring or a five or six membered ring with 1, 2, or 3 heteroatoms from the group including O, S, SO, $SO_2$ or $NR^5$; $R^F$ is H or optionally substituted alkyl, aryl, alkoxy, or aminoalkyl; $R^G$ is H, alkyl, or substituted alkyl; $R^5$ is H or alkyl; Q is O, S, $NR_6$, or $CR^7R^8$; $R^6$ is CN, $SO_2CF_3$, or optionally substituted alkyl, cycloalkyl, aryl, or heterocyclic ring; $R^7$ and $R^8$ are H, $NO_2$, CN $CO_2R^9$, or optionally substituted alkyl, cycloalkyl, aryl, or heterocyclic; $R^9$ is $C_1$ to $C_3$ alkyl; or $CR^7R^8$ form a six membered ring of the structure below:

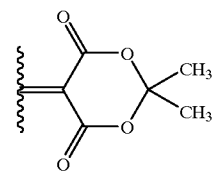

W is O or a chemical bond; or a pharmaceutically acceptable salt thereof, as well as their use and pharmaceutical compositions as agonists and antagonists of the progesterone receptor.

49 Claims, No Drawings

U.S. PATENT DOCUMENTS

| | | | |
|---|---|---|---|
| 5,007,952 A | 4/1991 | Kume et al. ................... | 71/73 |
| 5,171,851 A | 12/1992 | Kim et al. ..................... | 544/50 |
| 5,414,088 A | 5/1995 | Von Der Saal et al. ...... | 546/158 |
| 5,453,516 A | 9/1995 | Fischer et al. ............... | 548/543 |
| 5,475,020 A | 12/1995 | Johnson et al. ............. | 548/466 |
| 5,521,166 A | 5/1996 | Grubb ......................... | 514/170 |
| 5,681,817 A | 10/1997 | Hodgen et al. ............... | 514/12 |
| 5,688,808 A | 11/1997 | Jones et al. .................. | 514/285 |
| 5,688,810 A | 11/1997 | Jones et al. .................. | 514/311 |
| 5,693,646 A | 12/1997 | Jones et al. .................. | 514/285 |
| 5,693,647 A | 12/1997 | Jones et al. .................. | 514/285 |
| 5,696,127 A | 12/1997 | Jones et al. .................. | 514/285 |
| 5,696,130 A | 12/1997 | Jones et al. .................. | 514/291 |
| 5,696,133 A | 12/1997 | Pooley et al. ............... | 514/314 |
| 5,719,136 A | 2/1998 | Chwailisz et al. .......... | 514/170 |
| 5,733,902 A | 3/1998 | Schneider .................... | 514/177 |
| 5,808,139 A | 9/1998 | Pathirana .................... | 560/138 |
| 5,874,430 A | 2/1999 | Christ ...................... | 514/229.8 |
| 6,077,840 A | 6/2000 | Kurihara ................. | 514/232.8 |

FOREIGN PATENT DOCUMENTS

| | | |
|---|---|---|
| EP | 510235 | 10/1992 |
| EP | 947 507 | 10/1999 |
| EP | 978 279 | 2/2000 |
| JP | 63112584 | 5/1988 |
| WO | WO 86/03749 | 7/1986 |
| WO | WO 91/04974 | 4/1991 |
| WO | WO 91/06545 | 5/1991 |
| WO | WO 93/12085 | 6/1993 |
| WO | WO 94/14434 | 7/1994 |
| WO | WO 94/29272 | 12/1994 |
| WO | WO 95/11013 | 4/1995 |
| WO | WO 95/20389 | 8/1995 |
| WO | WO 95/20972 | 8/1995 |
| WO | WO 95/33746 | 12/1995 |
| WO | WO 96/15794 | 5/1996 |
| WO | WO 96/19458 | 6/1996 |
| WO | WO 96/19997 | 7/1996 |
| WO | WO 97/13767 | 4/1997 |
| WO | WO 97/49407 | 12/1997 |
| WO | WO 98/14436 | 4/1998 |
| WO | WO 98/27059 | 6/1998 |
| WO | WO 98/55116 | 12/1998 |
| WO | WO 99/10325 | 3/1999 |
| WO | WO 99/11264 | 3/1999 |
| WO | WO 99/15500 | 4/1999 |
| WO | WO 99/44608 | 9/1999 |

OTHER PUBLICATIONS

Kolasa, K., et al., "Preliminary Pharmacological Studies of the Central Action of Phenyl and Piperidinomethyl Derivatives of 2–Benzoxazolone." *Chemical Abstracts*, vol. 99, No. 1, Abst. No. 157a, Jul. 4, 1983.

Meanwell N.A., et al., "Regiospecific Functionalization of 1,3–dihydro–2H–Benzimidazol–2–One and Structurally Related Cyclic Urea Derivatives" *J. Organic Chem.*, 60(6): 1565–82 (Mar. 24, 1995).

Singh, B., et al., "An Efficient and Novel Synthesis of Fused Thiazol–2(3H)–ones" *Heterocycles*, 36(1): 133–134, p. 136, compounds 16a, 18a, Jan. 1993.

Vernin, G., et al., "Etude Dans la Serie des Radicaux Heterocycliques. Partie XV. Decomposition aprotique de 1' amino–6–ethyl–2–benzothiazole dans des substrats aromatiques et heteroaromatiques: preparation des mesityl–6– et furyl–6–ethyl–2–benzothiazoles, des sels quaternaires et des spiropyrannes correspondants" *Helvetica Chimica Acta*, 62(1/3):21–30 Jan. 24, 1979.

V.K. Jhalani et al., "A Convenient Synthesis of 5–Keto–6–methyl–5,6–dihydro–1,6–naphthridine", *Indian Journal of Chemistry*, 22B:916 (Sep. 1983).

R.M. Evans, "The Steroid and Thyroid Hormone Receptor Superfamily", *Science*, 240:889 (May 13, 1988).

A. Ulmann et al., "Clinical Uses of Mifepristone (MFP)", *Ann. N.Y. Acad. Sci.*, 261:248 (Jun. 12, 1995).

R. Kekkonen et al., "Sequential Regiment of the Antiprogesterone RU486 and Synthetic Progestin for Contraception", *Fertility and Sterility*, 60(4):610 (Oct. 1993).

K. Horwitz et al., "Progestin, Progesterone Receptors, and Breast Cancer", "Horm. Cancer", publisher: Birkhaeuser, Boston, Mass., ed. Vedeckis, p. 283–306 (1996) abstract only.

A. A. Murphy et al., "Regression of Uterine Leiomyomata in Response to the Antiprogesterone RU 486", *J. Clin. Endo. Metab.*, 76(2):513 (Feb. 1993).

L. M. Kettel et al., "Endocrine Responses to Long–Term Administration of the Antiprogesterone RU486 in Patients with Pelvic Endometriosis", *Fertility and Sterility*, 56(3):402 (Sep. 1991).

H. Michna et al., "Differentiation Therapy with Progesterone Antagonists", *Ann. N.Y. Acad. Sci.*, 761:224 (Jun. 1995).

L. Zhi et al., "5–Aryl–1,2–Dihydrochromeno[3,4–f]quinolines: A Novel Class of Nonsteroidal Human Progesterone Receptor Agonists", *J. Med. Chem.*, 41(3):291 (Oct. 22, 1998).

D. W. Combs et al., "Nonsteroidal Progesterone Receptor Ligands. 2. High–Affinity Ligands with Selectivity for Bone Cell Progesterone Receptors", *J. Med. Chem.*, 38:4880 (Dec. 8, 1995).

K. L. Perlman et al., "20–Oxopregnacalciferols: Vitamin D Compounds that Bind the Progesterone Receptor", *Tet. Letters*, 35(15):2295 (1994).

L. G. Hamann et al., "Synthesis and Biological Activity of Novel Nonsteroidal Progesterone Receptor Antagonists", *Ann. N.Y. Acad. Sci.*, 761:383 (Jun. 12, 1995).

R. H. K. Chen et al., "Synthesis and SAR of a Novel Series of Spirobenzothlzaepine Derivatives with Antiprogestin Activity", POI–37, 16$^{th}$ Int. Cong. Het. Chem., Montana (1997).

B. Narr et al., "Preparation, Testing, and Formulation of Imidazobenzoxazinones as Cardiotonics", *Chemical Abstracts*, 109:22973 (1988).

R. J. Hartmann et al., "Effects of Brofoxine, A New Anxiolytic on Experimentally Induced Conflict in Rats", *Proc West. Pharmacol. Soc.*, 21:51–55 (1978).

B. Singh et al., "Novel cAMP PDE III Inhibitor: Imidazo [4,5–b]pyridin–2(3H)–ones and Thiazolo[4,5–b] pyridin–2(3H)–ones and Their Analogs", *J. Med. Chem.*, 37:248 (Jan. 21, 1994).

A. Andreani et al., "Potential Antitumor Agents XVII (1). Cytotoxic Agents from Indole Derivatives and Their Intermediates", *Acta. Pharm. Nord.*, 2(6):407 (1990).

Sakata et al., "Silver Halide Photographic Materials Useful for Platemaking", *Chemical Abstracts*, 123:301431 (1993).

P. Pflegel et al., "Polarografie con 7–Chlor–5–phenyl–2–thioxo–1H–2,3–dihydro–1,3,4–benzotriazepinen", *Pharmazie*, 37(10): 714–717 (1982).

E. I. Barengolts et al., "Progesterone Antagonist RU 486 Has Bone–Sparing Effects in Ovariectomized Rats", *Bone*, 17(1):21 (Jul. 1995).

E. V. Gromachevskaya et al., "Studies of 4H–3, 1–Benzoxazines", *Chem. Heterocyl. Cmpds.* 33(10):1209–1214 (1997).

D. Chiarino et al., "2, 1–Benzisothiazoline 2, 2–Dioxide and Derivatives", *J. Heterocycl. Chem.*, 23(6):1645–1649 (Nov.– Dec. 1986).

A. Turck et al., "On the Metabolism of 3–Substituted and 3,6–Disubstituted Pyridazines", *Tetrahedron*, 49(3):599–606 (1993).

V. Kumar et al., "Synthesis of 7–Azaindole and 7–Azaoxindole Derivatives through a Palladium–Catalyzed Cross–Coupling Reaction", *J. Org. Chem.*, 57(25):6995–6998 (1992).

P. Canonne et al., "Spirocyclization of 1–(o–Aminophenyl) cycloalkanols and 1–(2'–Amino–3'–pyridinyl)cycloalkanols", *J. Heterocyclic Chem.*, 26:113 (Jan.–Feb. 1989).

M–C. Forest et al., "A Novel Class of Cardiotonic Agents: Synthesis and Biological Evaluation of 5–Substituted 3,6–Dihydrothiadiazin–2–ones with Cyclic AMP Phosphodiesterase Inhibiting and Myofibrillar Calcium Sensitizing Properties", *J. Med. Chem.*, 35:163–172 (Jan. 1992).

D. W. Combs et al., "Heteroatom Analogues of Bemoradan: Chemistry and Cardiotonic Activity of 1, 4–Benzothiazinylpyridazinones", *J. Med. Chem.*, 35:172–176 (Jan. 1992).

Kurihara et al., "Synthesis of (±)–PF1092A, B, and C; New Nonsteroidal Progesterone Receptor Ligands", *J. Antibiotics*, 50(4):360 (Apr. 1997).

A. Kende et al., "Regioselective C–3 Alkylation of Oxindole Dianion", *Synth. Commun.* 12(1):1 (1982).

T. Tucker et al., "Synthesis of a Series of 4–(Arylethylnyl)–6–Chloro–4–Cyclopropyl–3, 4–dihydroquinazolin–2(1H)–ones as Novel Non–Nucleoside HIV–1 Reverse Transcriptase Inhibitors", *J. Med. Chem.*, 37:2347–2444 (Jul. 22, 1994).

J. P. Edwards et al., "5–Aryl–1,2–Dihydro–5H–Chromeno [3,4–f]Quinolines as Potent, Orally Active, Nonsteroidal Progesterone Receptor Agonists: The Effect of D–Ring Subsituents", *J. Med. Chem.*, 41:303–310 (Jan. 29, 1998).

\* cited by examiner

CYCLIC UREA AND CYCLIC AMIDE DERIVATIVES

CROSS-REFERENCE TO RELATED APPLICATION

This application claims the benefit of the priority of U.S. Provisional Patent Application No. 60/183,037, filed May 4, 1999.

FIELD OF THE INVENTION

This invention relates to compounds which are agonists and antagonists of the progesterone receptor, their preparation and utility.

BACKGROUND OF THE INVENTION

Intracellular receptors (IR) form a class of structurally related gene regulators known as "ligand dependent transcription factors" (R. M. Evans, Science, 240, 889, 1988). The steroid receptor family is a subset of the IR family, including progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA the complex modulates the production of mRNA and protein encoded by that gene.

A compound that binds to an IR and mimics the action of the natural hormone is termed an agonist, whilst a compound that inhibits the effect of the hormone is an antagonist.

PR agonists (natural and synthetic) are known to play an important role in the health of women. PR agonists are used in birth control formulations, typically in the presence of an ER agonist. ER agonists are used to treat the symptoms of menopause, but have been associated with a proliferative effect on the uterus that can lead to an increased risk of uterine cancers. Co-administration of a PR agonist reduces or ablates that risk.

PR antagonists may also be used in contraception. In this context they may be administered alone (Ulmann, et al, Ann. N.Y. Acad. Sci., 261, 248, 1995), in combination with a PR agonist (Kekkonen, et al, Fertility and Sterility, 60, 610, 1993) or in combination with a partial ER antagonist such as tamoxifen (WO 96/19997 A1, Jul. 4, 1996).

PR antagonists may also be useful for the treatment of hormone dependent breast cancers (Horwitz, et al, Horm. Cancer, 283, pub: Birkhaeuser, Boston, Mass., ed. Vedeckis) as well as uterine and ovarian cancers. PR antagonists may also be useful for the treatment of non-malignant chronic conditions such as fibroids (Murphy, et al, J. Clin. Endo. Metab., 76, 513, 1993) and endometriosis (Kettel, et al, Fertility and Sterility, 56, 402, 1991).

PR antagonists may also be useful in hormone replacement therapy for post menopausal patients in combination with a partial ER antagonist such as tamoxifen (U.S. Pat. No. 5,719,136).

PR antagonists, such as mifepristone and onapristone, have been shown to be effective in a model of hormone dependent prostate cancer, which may indicate their utility in the treatment of this condition in men (Michna, et al, Ann. N.Y. Acad. Sci., 761, 224, 1995).

The compounds of this invention have been shown to act as competitive inhibitors of progesterone binding to the PR and act as agonist and/or antagonists in functional models, either/or in-vitro and in-vivo. These compounds may be used for contraception, in the treatment of fibroids, endometriosis, breast, uterine, ovarian and prostate cancer, and post menopausal hormone replacement therapy.

Jones, et al, (U.S. Pat. No. 5,688,810) describe the PR antagonist dihydroquinoline 1.

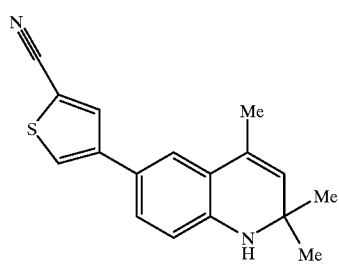

Jones, et al, described the enol ether 2 (U.S. Pat. No. 5,693,646) as a PR ligand.

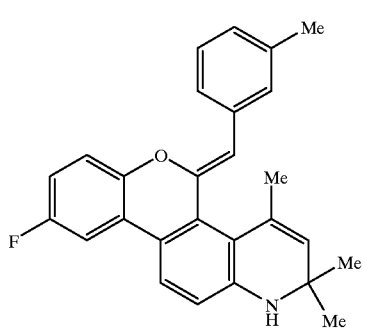

Jones, et al, described compound 3 (U.S. Pat. No. 5,696,127) as a PR ligand.

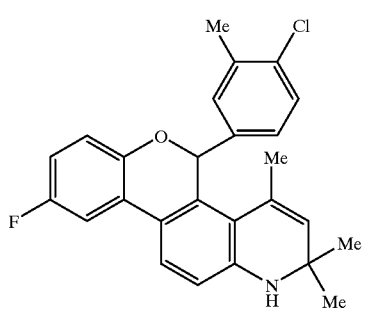

Zhi, et al, described lactones 4, 5 and 6 as PR antagonists (J. Med. Chem., 41, 291, 1998).

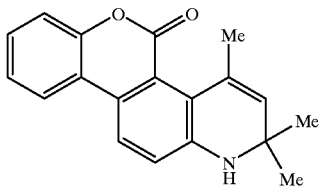

Zhi, et al, described the ether 7 as a PR antagonist (J. Med. Chem, 41, 291, 1998).

Combs, et al., disclosed the amide 8 as a ligand for the PR (*J. Med. Chem.*, 38, 4880, 1995).

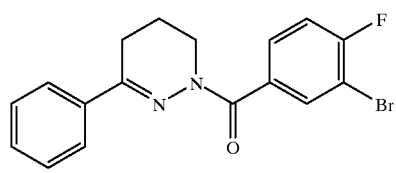

Perlman, et. al., described the vitamin D analog 9 as a PR ligand (*Tet. Letters,* 35, 2295, 1994).

Hamann, et al, described the PR antagonist 10 (*Ann. N Y Acad. Sci.,* 761, 383, 1995).

Chen, et al, described the PR antagonist 11 (Chen, et al, POI-37, 16th Int. Cong. Het. Chem., Montana, 1997).

Kurihari, et. al., described the PR ligand 12 (*J. Antibiotics,* 50, 360, 1997).

The patent by Christ et al. (WO 9814436) claims a cyclo amide such as compound A as inhibitors of HIV reverse transciptase. Other prior art includes pyridazine cyclo amide such as compound B by Turck et al. (*Tetrahedron,* 49(3), 599–606 (1993)) and compounds such as C by Canonne et al. (*J. heterocyclic Chem.* 26, 113(1989)). No activity data were reported in Turck's and Canonne' publications.

A
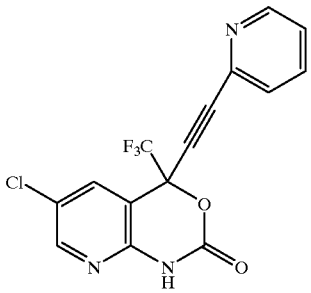

B
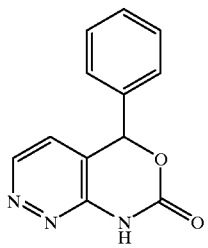

C
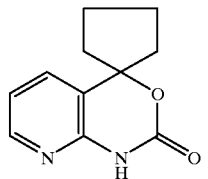

Regarding cyclic amides, Singh et al. and Kumar et al. (Singh et al. *J. Med. Chem.* 37(2), 248–254(1994); Kumar et al. *J. Org. Chem.* 57(25), 6995–6998(1992)) disclose compounds such as D and E claimed as cAMP PDE III inhibitors.

D
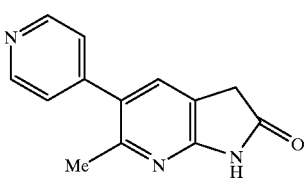

E
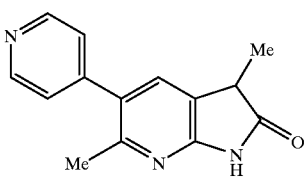

DESCRIPTION OF THE INVENTION

This invention provides compounds of Formula I:

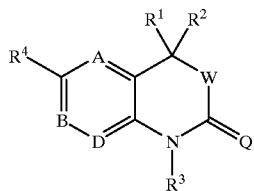

wherein:

A, B and D are N or CH, with the proviso that A, B and D can not all be CH;

$R^1$ and $R^2$ are independent substituents selected from H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, $NR^B$-$COR^A$;

or $R^1$ and $R^2$ are fused to form a spirocyclic ring selected from a), b) or c), each spirocyclic ring optionally substituted by from 1 to 3 $C_1$–$C_3$ alkyl groups:

a) a 3 to 8 membered spirocyclic alkyl ring;
  b) a 3 to 8 membered spirocyclic alkenyl ring; or
  c) an optionally substituted 3 to 8 membered heterocyclic ring containing one to three heteroatoms from the group including O, S and N; the spirocyclic rings of a), b) and c) being optionally substituted by from 1 to 4 groups selected from fluorine, $C_1$ to $C_6$ alkyl, $C_1$ to $C_6$ alkoxy, $C_1$ to $C_6$ thioalkyl, —$CF_3$, —OH, —CN, $NH_2$, —NH($C_1$ to $C_6$ alkyl), or —N($C_1$ to $C_6$ alkyl)$_2$;

$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^B$ is H, $C_1$ to $C_3$ alkyl, or substituted $C_1$ to $C_3$ alkyl;

$R^3$ is H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, or $COR^C$;

$R^C$ is H, $C_1$ to $C_3$ allyl, substituted $C_1$ to $C_3$ allyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^4$ is a trisubstituted benzene ring containing the substituents X, Y and Z as shown below:

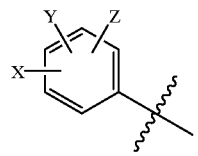

X is taken from the group including halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring containing 1 to 3 heteroatoms, $COR^D$, $OCOR^D$, or $NR^ECOR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl,

Y and Z are independent substituents taken from the group including H, halogen, CN, $NO_2$, $C_1$ to $C_3$ alkoxy, $C_1$ to $C_3$ alkyl, or $C_1$ to $C_3$ thioalkoxy;

or $R^4$ is a five or six membered ring with 1, 2, or 3 heteroatoms from the group including O, S, SO, $SO_2$ or $NR^5$ and containing one or two independent substituents from the group including H, halogen, CN, $NO_2$ and $C_1$ to $C_3$ alkyl, $C_1$ to $C_3$ alkoxy, $C_1$ to $C_3$ aminoalkyl, $COR^F$, or $NR^GCOR^F$;

$R^F$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^G$ is H, $C_1$ to $C_3$ alkyl, or substituted $C_1$ to $C_3$ alkyl;

$R^5$ is H or $C_1$ to $C_3$ alkyl;

Q is O, S, $NR^6$, or $CR^7R^8$;

$R_6$ is from the group including CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, or $SO_2CF_3$;

$R^7$ and $R^8$ are independent substituents from the group including H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN, or $CO_2R^9$;

$R^9$ is $C_1$ to $C_3$ alkyl;

or $CR^7R^8$ form a six membered ring of the structure below:

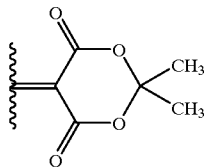

W is O or a chemical bond.

When W is a chemical bond, it is understood that Formula I exists as:

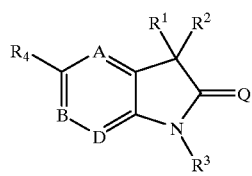

Preferred compounds are those of Formula I

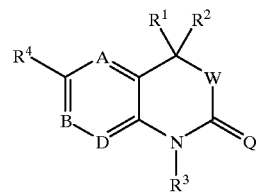

wherein:

A, B and D are N or CH, with the proviso that A, B and D can not all be CH;

$R^1$ is H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$;

$R^2$ is H, $C_1$ to $C_6$ alkyl, substituted $C_1$ to $C_6$ alkyl, $C_2$ to $C_6$ alkenyl, substituted $C_2$ to $C_6$ alkenyl, $C_3$ to $C_8$ cycloalkyl, substituted $C_3$ to $C_8$ cycloalkyl, aryl, substituted aryl, heterocyclic, substituted heterocyclic, $COR^A$, or $NR^BCOR^A$, or $R^1$ and $R^2$ are fused to form the optionally substituted 3 to 8 membered spirocyclic allyl, alkenyl or heterocyclic rings described above;

$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^B$ is H, $C_1$ to $C_3$ alkyl, or substituted $C_1$ to $C_3$ alkyl;

$R^3$ is H, OH, $NH_2$, $C_1$ to $C_6$ alkyl, substituted $C_1$ to $C_6$ alkyl, $C_3$ to $C_6$ alkenyl, substituted $C_1$ to $C_6$ alkenyl, or $COR^C$;

$R^C$ is H, $C_1$ to $C_4$ alkyl, substituted $C_1$ to $C_4$ alkyl, aryl, substituted aryl, $C_1$ to $C_4$ alkoxy, substituted $C_1$ to $C_4$ alkoxy, $C_1$ to $C_4$ aminoalkyl, or substituted $C_1$ to $C_4$ aminoalkyl;

$R^4$ is a trisubstituted benzene ring containing the substituents X, Y and Z as shown below:

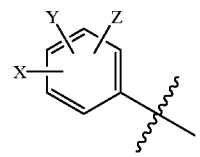

X is selected from halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkoxy, substituted $C_1$ to $C_3$ thioalkoxy, $C_1$ to $C_3$ aminoalkyl, substituted $C_1$ to $C_3$ aminoalkyl, $NO_2$, $C_1$ to $C_3$ perfluoroalkyl, a 5 membered heterocyclic ring containing 1 to 3 heteroatoms, $COR^D$, $OCOR^D$, or $NR^ECOR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoakyl, or substituted $C_1$ to $C_3$ aminoalkyl;

$R^E$ is H, $C_1$ to $C_3$ alkyl, or substituted $C_1$ to $C_3$ alkyl;

Y and Z are independent substituents selected from H, halogen, CN, $NO_2$, $C_1$ to $C_3$ alkoxy, $C_1$ to $C_3$ alkyl, or $C_1$ to $C_3$ thioalkoxy; or $R^5$ is a five or six membered ring with 1, 2, or 3 heteroatoms from the group including O, S, SO, $SO_2$ or $NR^5$ and containing one or two independent substituents from the group including H, halogen, CN, $NO_2$ and $C_1$ to $C_3$ alkyl, or $C_1$ to $C_3$ alkoxy;

$R^5$ is H or $C_1$ to $C_3$ alkyl;

Q is O, S, $NR^6$, or $CR^7R^8$;

$R_6$ is selected from CN, $C_1$ to $C_6$ alkyl, substituted $C_1$ to $C_6$ allyl, $C_3$ to $C_8$ cycloalkyl, substituted $C_3$ to $C_8$ cycloalkyl, aryl, substituted aryl, heterocyclic, substituted heterocyclic, or $SO_2CF_3$;

$R^7$ and $R^8$ are independent substituents from the group including H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN, or $CO_2R^9$;

$R^9$ is $C_1$ to $C_3$ alkyl;

or $CR^7R^8$ form a six membered ring of the structure below:

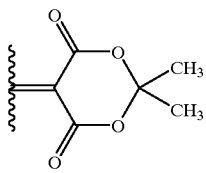

W is O or a chemical bond;

or a pharmaceutically acceptable salt thereof Still, more preferred compounds are those of Formula I

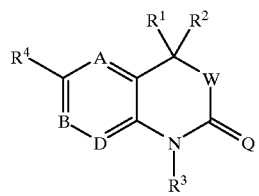

wherein:

A, B and D are N or CH, with the proviso that A, B and D cannot all be CH;

$R^1=R^2$ and are selected from the group of $C_1$ to $C_3$ alkyl, substituted $C_1$ to $C_3$ alkyl, or spirocyclic alkyl constructed by fusing $R_1$ and $R^2$ to form a 3 to 6 membered spirocyclic ring;

$R^3$ is H, OH, $NH_2$, $C_1$ to $C_6$ alkyl, substituted $C_1$ to $C_6$ alkyl, or $COR^C$;

$R^C$ is H, $C_1$ to $C_4$ alkyl, or $C_1$ to $C_4$ alkoxy;

$R^4$ is a disubstituted benzene ring containing the substituents X, and Y as shown below:

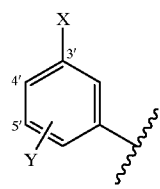

X is selected from the group of halogen, CN, $C_1$ to $C_3$ alkoxy, $C_1$ to $C_3$ alkyl, $NO_2$, $C_1$ to $C_3$ perfluoroalkyl, 5 membered heterocyclic ring containing 1 to 3 heteroatoms, or $C_1$ to $C_3$ thioalkoxy;

Y is a substituent on the 4' or 5'position from the group including H, halogen, CN, $NO_2$, $C_1$ to $C_3$ alkoxy, $C_1$ to $C_4$ alkyl, or $C_1$ to $C_3$ thioalkoxy; or $R^4$ is a five membered ring with the structure:

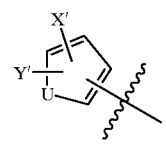

U is O, S, or $NR^5$;

$R^5$ is H, or $C_1$ to $C_3$ alkyl, or $C_1$ to $C_4$ $CO_2$alkyl;

X' is selected from halogen, CN, $NO_2$, $C_1$ to $C_3$ alkyl, or $C_1$ to $C_3$ alkoxy;

Y' is selected from H and $C_1$ to $C_4$ alkyl;

or $R^4$ is a six membered ring with the structure:

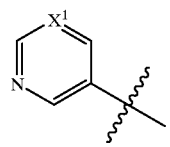

$X^1$ is N or $CX^2$;

$X^2$ is halogen, CN or $NO_2$;

Q is O, S, $NR^6$, or $CR^7R^8$;

$R_6$ is selected from CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, or $SO_2CF_3$;

$R^7$ and $R^8$ are independent substituents selected from H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN, or $CO_2R^9$;

$R^9$ is $C_1$ to $C_3$ alkyl;

or $CR^7R^8$ form a six membered ring of the structure below:

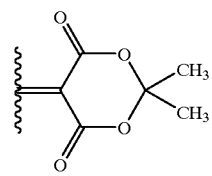

or a pharmaceutically acceptable salt thereof.

Further preferred compounds include those of Formula I:

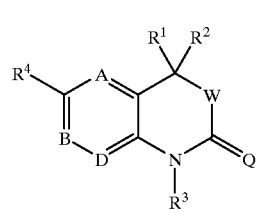

wherein:

A, B and D are N or CH, with the proviso that A, B and D can not all be CH;

$R^1=R^2$ and are selected from $CH_3$ and spirocyclic alkyl constructed by fusing $R^1$ and $R^2$ to form a 6 membered spirocyclic ring;

$R^3$ is H, OH, $NH_2$, $CH_3$, substituted methyl, or $COR^C$;
$R^C$ is H, $C_1$ to $C_3$ alkyl, or $C_1$ to $C_4$ alkoxy;
$R^4$ is a disubstituted benzene ring containing the substituents X and Y as shown below:

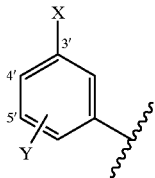

X is halogen, CN, methoxy, $NO_2$, or 2-thiazole;
Y is a substituent on the 4' or 5' position selected from H and F;
or
$R^4$ is a five membered ring of the structure:

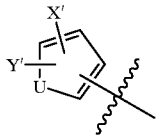

U is O, S, or NH;
X' is halogen, CN, or $NO_2$;
Y' is H or $C_1$ to $C_4$ alkyl;
Q is O, S, $NR^6$, or $CR^7R^8$;
$R_6$ is CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, or $SO_2CF_3$;
$R^7$ and $R^8$ are independent substituents selected from H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN, or $CO_2R^9$;
$R^9$ is $C_1$ to $C_3$ alkyl;
or $CR^7R^8$ form a six membered ring of the structure:

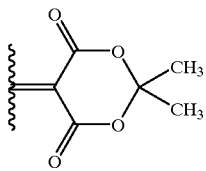

W is O or a chemical bond;
or a pharmaceutically acceptable salt thereof.

Each of the generic and subgeneric groups of compounds described above, as well as the methods of treatment and pharmaceutical compositions utilizing them, may be divided into two further subgeneric groups, one in which Q is oxygen and another in which Q is sulfur or $NR^6$ or $CR^7R^8$.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

The term "alkyl" is used herein to refer to both straight- and branched-chain saturated aliphatic hydrocarbon groups having one to eight carbon atoms, preferably one to six carbon atoms; "alkenyl" is intended to include both straight- and branched-chain alkyl group with at least one carbon-carbon double bond and two to eight carbon atoms, preferably two to six carbon atoms; "alkynyl" group is intended to cover both straight- and branched-chain alkyl group with at least one carbon-carbon triple bond and two to eight carbon atoms, preferably two to six carbon atoms.

The terms "substituted alkyl", "substituted alkenyl", and "substituted alkynyl" refer to alkyl, alkenyl, and alkynyl as just described having one or more substituents from the group including halogen, CN, OH, $NO_2$, amino, aryl, heterocyclic, substituted aryl, substituted heterocyclic, alkoxy, aryloxy, substituted alkyloxy, alkylcarbonyl, alkylcarboxy, alkylamino, arylthio. These substituents may be attached to any carbon of an alkyl, alkenyl, or alkynyl group provided that the attachment constitutes a stable chemical moiety.

The term "aryl" is used herein to refer to an aromatic system which may be a single ring or multiple aromatic rings fused or linked together as such that at least one part of the fused or linked rings forms the conjugated aromatic system. The aryl groups include but are not limited to phenyl, naphthyl, biphenyl, anthryl, tetrahydronaphthyl, and phenanthryl.

The term "substituted aryl" refers to aryl as just defined having one to four substituents from the group including halogen, CN, OH, $NO_2$, amino, alkyl, cycloalkyl, alkenyl, alkynyl, alkoxy, aryloxy, substituted alkyloxy, alkylcarbonyl, alkylcarboxy, alkylamino, or arylthio.

The term "heterocyclic" is used herein to describe a stable 4- to 7-membered monocyclic or a stable multicyclic heterocyclic ring which is saturated, partially unsaturated, or unsaturated, and which consists of carbon atoms and from one to four heteroatoms selected from the group including N, O, and S atoms. The N and S atoms may be oxidized. The heterocyclic ring also includes any multicyclic ring in which any of the above defined heterocyclic rings is fused to an aryl ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, and isoquinolinyl.

The term "substituted heterocyclic" is used herein to describe the heterocyclic just defined having one to four substituents selected from the group which includes halogen, CN, OH, $NO_2$, amino, alkyl, substituted alkyl, cycloalkyl, alkenyl, substituted alkenyl, alkynyl, alkoxy, aryloxy, substituted alkyloxy, alkylcarbonyl, alkylcarboxy, alkylamino, or arylthio. The term "alkoxy" is used herein to refer to the OR group, where R is an alkyl or substituted alkyl. The term "aryloxy" is used herein to refer to the OR group, where R is an aryl or substituted aryl. The term "alkylcarbonyl" is used herein to refer to the RCO group, where R is an alkyl or substituted alkyl. The term "alkylcarboxy" is used herein to refer to the COOR group, where R is an alkyl or substituted alkyl. The term "aminoalkyl" refers to both secondary and tertiary amines wherein the alkyl or substituted alkyl groups contain one to eight carbon atoms, which may be either same or different and the point of attachment is on the nitrogen atom. "Halogen" refers to Cl, Br, F, or I.

The compounds of the present invention can be used in the form of salts derived from pharmaceutically or physiologically acceptable acids or bases. These salts include, but are not limited to, the following salts with inorganic acids such as hydrochloric acid, sulfuric acid, nitric acid, phosphoric acid and, as the case may be, such organic acids as acetic acid, oxalic acid, succinic acid, and maleic acid. Other salts include salts with alkali metals or alkaline earth metals, such as sodium, potassium, calcium or magnesium in the form of esters, carbamates and other conventional "prodrug" forms, which, when administered in such form, convert to the active moiety in vivo.

The compounds of this invention have been shown to act as competitive inhibitors of progesterone binding to the PR and act as agonist and/or antagonists in functional models, either/or in-vitro and in-vivo. These compounds may be used for contraception, in the treatment of fibroids, endometriosis, breast, uterine, ovarian and prostate cancer, and post menopausal hormone replacement therapy.

This invention includes pharmaceutical compositions and treatments which comprise administering to a mammal a pharmaceutically effective amount of one or more compounds as described above wherein Q is oxygen as antagonists of the progesterone receptor. The invention further provides comparable methods and compositions which utilize one or more compounds herein wherein Q is S, $NR^6$, or $CR^7R^8$ as agonists of the progesterone receptor.

The progesterone receptor antagonists of this invention, used alone or in combination, can be utilized in methods of contraception and the treatment and/or prevention of benign and malignant neoplastic disease. Specific uses of the compounds and pharmaceutical compositions of invention include the treatment and/or prevention of uterine myometrial fibroids, endometriosis, benign prostatic hypertrophy; carcinomas and adenocarcinomas of the endometrium, ovary, breast, colon, prostate, pituitary, meningioma and other hormone-dependent tumors. Additional uses of the present progesterone receptor antagonists include the synchronization of the estrus in livestock.

The progesterone receptor agonists of this invention, used alone or in combination, can be utilized in methods of contraception and the treatment and/or prevention of dysfunctional bleeding, uterine leiomyomata, endometriosis; polycystic ovary syndrome, carcinomas and adenocarcinomas of the endometrium, ovary, breast, colon, prostate. Additional uses of the invention include stimulation of food intake.

When the compounds are employed for the above utilities, they may be combined with one or more pharmaceutically acceptable carriers or excipients, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in a sustained release form. For most large mammals, the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvents customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The compounds of this invention can be prepared following the Schemes illustrated below:

As demonstrated in Scheme I, the compounds of this invention are generally prepared by employing the suitable coupling reaction as a final step. An appropriately substituted ortho-amino acid or its derivatives such as an ethyl ester (X=Br, I, Cl, or a latent coupling precursor such as alkoxy group which can be converted into an OTf group suitable in the coupling reaction) is treated with a suitable organo metallic reagent, e.g. Grignard reagent, in appropriate nonprotic solvents which include but not limited to THF or ether to give ortho-amino carbinol 2 under an inert atmosphere such as argon or nitrogen at −78° C. to room temperature. Ring closure of carbinol 2 to yield oxazin-2-ones 3 is commonly effected by a condensing agent such as carbonyldiimidazole, phosgene, dimethylcarbonate, or diethylcarbonate in a suitable nonprotic solvent such as THF at temperatures ranging from room temperature to 65° C. The arylation of oxazin-2-ones 3 to yield 4 can be effected by various coupling reactions including Suzuki, Stille reactions etc. These reactions are commonly performed in the presence of a transition metallic catalyst, e.g., palladium or nickel complex often with phosphino ligands, e.g., $Ph_3P$, 1,1'-bis(diphenylphosphino)ferrocene, 1,2-bis (diphenylphosphino)ethane or palladium salt such as palladium acetate. Under this catalytic condition, an appropriately substituted nucleophilic reagent, e.g., aryl boronic acid, arylstannane, or aryl zinc compound, is coupled with oxazinones 3 to give compounds 4. If a base is needed in the reaction, the commonly used bases include but not limited to sodium bicarbonate, sodium carbonate, potassium phosphate, barium carbonate, potassium acetate, or cesium fluoride. The most commonly used solvents in these reactions include benzene, DMF, isopropanol, ethanol, DME, ether, acetone or a mixture of any one of these solvent and water. The coupling reaction is generally executed under an inert atmosphere such as nitrogen or argon at temperatures ranging from room temperature to 95° C. Oxazinones 3 can be converted into a nucleophile such as boronic acid which can be coupled with an appropriate electrophile, e.g., aryl bromide or aryl iodide, to yield 6 employing the coupling reaction condition as described above.

Scheme I

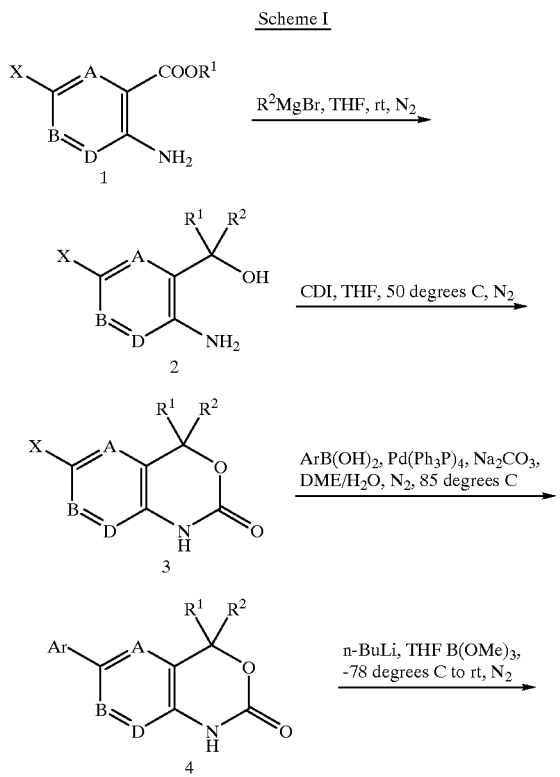

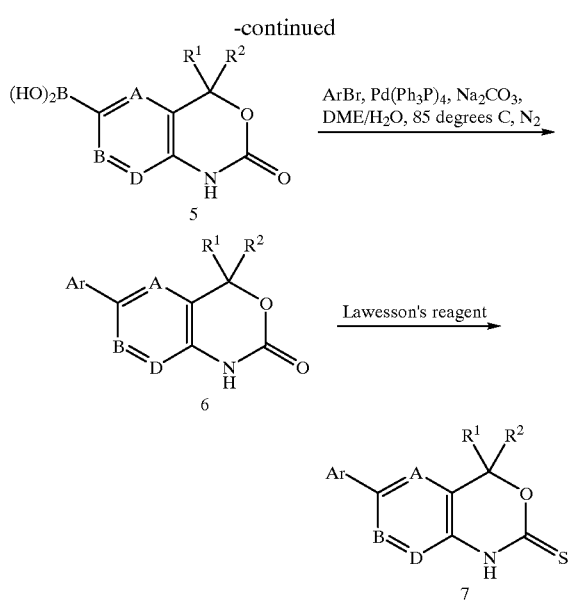

The transformation of 3 into 5 can be effected by treating 3 with an organo metallic reagent, e.g., n-BuLi, in a nonprotic solvent such as THF or ether followed by quenching the reaction solution with a suitable electrophile such as trimethyl borate, triisopropyl borate, bishexalkyl tin reagent, or zinc chloride at temperatures ranging from −78° C. to room temperature under an inert atmosphere such as argon or nitrogen. Conversion of carbamate 6 to thiocarbamate 7 can be readily effected by treatment of 6 with a suitable sulfur reagent such as $P_2S_5$ or Lawesson's reagent in a suitable non-protic solvent such as toluene, chlorobenzene, benzene, or xylene under an inert atmosphere such as argon or nitrogen at the temperature of boiling solvent.

Scheme II describes the procedures to prepare oxazinones bearing two different substituents at position-4. The Weinreb amide 9 can be prepared from an appropriately substituted isatoic anhydride when treated with N—, O-dimethylhydroxyl-amine hydrochloride salt in a protic solvent such as ethanol or isopropanol at reflux under an inert atmosphere such as argon or nitrogen. Coupling of amide 9 with an aryl electrophile such as aryl boronic acid or arylstannane to give 10 can be effected by employing a typical coupling reaction such as Suzuki, Stille coupling procedure in a similar fashion as described for the preparation of oxazinones 4. Treatment of Weinreb amide 10 with organo metallic compounds, e.g., alkyllithium, alkynyllithium, aryllithium, or their Grignard counterpart in a nonprotic solvent such as THF or ether under an inert atmosphere such as argon or nitrogen at −78° to room temperature affords amino ketone 11. Conversion of ketone 11 to carbinol 12 can be effected by treatment of 10 with an organo metallic reagent such as alkyl, alkynyl, or aryl Grignard compound in a nonprotic solvent such as THF or ether under an inert atmosphere such as argon or nitrogen at −78° C. to room temperature. Conversion of ketone 11 to carbinol 12 can also be effected by reduction of ketone group of 11 to the carbinol moiety of 12 using an appropriate reducing reagent such as lithium aluminum hydride, sodium borohydride in a suitable solvent such as THF, ether, or anhydrous alcohol under an inert atmosphere in the temperature ranging from 0° C. to the boiling point of the solvent. Ring closure of carbinol 12 to produce the compounds of this invention, 13, can be accomplished with condensing agents such as carbonyldiimidazole, phosgene, dimethylcarbonate, or diethylcarbonate in a suitable nonprotic solvent such as THF at temperatures ranging from room temperature to 65° C. Conversion of carbamate 13 to thiocarbamate 14 can be readily effected by treatment of 13 with a suitable sulfur reagent such as $P_2S_5$ or Lawesson's reagent in a suitable nonprotic solvent such as toluene, chlorobenzene, benzene, or xylene under an inert atmosphere such as argon or nitrogen at the temperature of boiling solvent.

ranging from −78° C. to room temperature as illustrated in Scheme III. Nitrile 16 can be readily prepared from an appropriately substituted nitrile such as bromobenzonitrile 15 using a suitable coupling reaction such as Stille or Suzuki protocol carried out in a similar fashion as described for the preparation of the Weinreb amide 10.

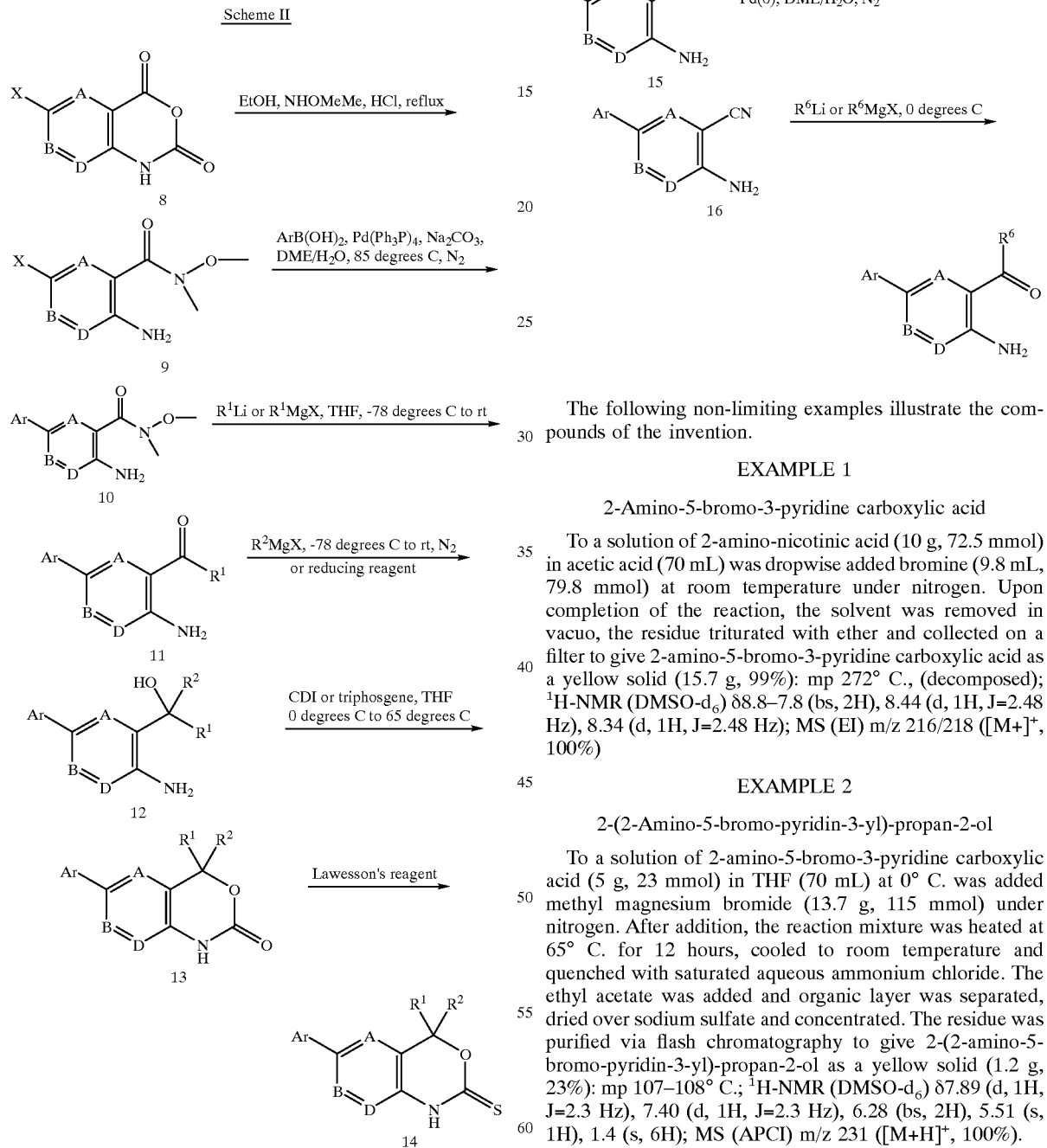

Alternatively, ortho-amino ketone 11 can be prepared by treatment of ortho-amino nitrile 16 with an organo metallic compound such as an organo lithium reagent or Grignard reagent in a suitable solvent such as THF or ether under an inert atmosphere such as argon or nitrogen at temperatures The following non-limiting examples illustrate the compounds of the invention.

EXAMPLE 1

2-Amino-5-bromo-3-pyridine carboxylic acid

To a solution of 2-amino-nicotinic acid (10 g, 72.5 mmol) in acetic acid (70 mL) was dropwise added bromine (9.8 mL, 79.8 mmol) at room temperature under nitrogen. Upon completion of the reaction, the solvent was removed in vacuo, the residue triturated with ether and collected on a filter to give 2-amino-5-bromo-3-pyridine carboxylic acid as a yellow solid (15.7 g, 99%): mp 272° C., (decomposed); $^1$H-NMR (DMSO-$d_6$) δ8.8–7.8 (bs, 2H), 8.44 (d, 1H, J=2.48 Hz), 8.34 (d, 1H, J=2.48 Hz); MS (EI) m/z 216/218 ([M+]$^+$, 100%)

EXAMPLE 2

2-(2-Amino-5-bromo-pyridin-3-yl)-propan-2-ol

To a solution of 2-amino-5-bromo-3-pyridine carboxylic acid (5 g, 23 mmol) in THF (70 mL) at 0° C. was added methyl magnesium bromide (13.7 g, 115 mmol) under nitrogen. After addition, the reaction mixture was heated at 65° C. for 12 hours, cooled to room temperature and quenched with saturated aqueous ammonium chloride. The ethyl acetate was added and organic layer was separated, dried over sodium sulfate and concentrated. The residue was purified via flash chromatography to give 2-(2-amino-5-bromo-pyridin-3-yl)-propan-2-ol as a yellow solid (1.2 g, 23%): mp 107–108° C.; $^1$H-NMR (DMSO-$d_6$) δ7.89 (d, 1H, J=2.3 Hz), 7.40 (d, 1H, J=2.3 Hz), 6.28 (bs, 2H), 5.51 (s, 1H), 1.4 (s, 6H); MS (APCI) m/z 231 ([M+H]$^+$, 100%).

EXAMPLE 3

6-Bromo-4,4'-dimethyl-1,4-dihydro-3-oxa-1,8-diaza-naphthalen-2-one

A mixture of 2-(2-amino-5-bromo-pyridin-3-yl)-propan-2-ol (0.86 g, 3.7 mmol) and 1,1'-carbonyldiimidazole (excess) in THF (10 mL) was heated at 35° C. overnight. The reaction solution was cooled to room temperature, poured into ethyl acetate (200 mL), washed with 1 N HCl (2×50 mL), dried over sodium sulfate, and concentrated. The residue was purified by a flash chromatography (silica gel, 25% ethyl acetate/hexane) to afford 6-bromo-4,4'-dimethyl-1,4-dihydro-3-oxa-1,8-diaza-naphthalen-2-one (0.9 g, 94%) as a white solid: mp 251–252° C.; $^1$H-NMR (DMSO-d$_6$) δ10.9 (s, 1H), 8.32 (d, 1H, J=2.19 Hz), 8.0 (d, 1H, J=2.22 Hz), 1.6 (s, 6H); MS (EI) m/z 256 ([M]$^+$, 80%); Anal. Calc. For C$_9$H$_9$BrN$_2$O$_2$: C, 42.05; H, 3.53; N, 10.90. Found: C, 42.15; H, 3.65; N, 10.80.

EXAMPLE 4

6-(3-Chloro-phenyl)-4,4-dimethyl-1,4-dihydro-3-oxa-1,8-diaza-naphthalene-2-one

A mixture of 6-bromo-4,4'-dimethyl-1,4-dihydro-3-oxa-1,8-diaza-naphthalen-2-one (0.1 g, 0.39 mmol), 3-chlorophenyl boronic acid (0.075 g, 0.47 mmol), tetrakis (triphenylphosphine)-palladium (0) (0.023 g, 0.02 mmol), and sodium carbonate (0.1 g, 0.94 mmol) in DME (8 mL) and water (5 mL) was subject to a blanket of nitrogen for 15 minutes at 50° C. and then was heated at 85° C. for 30 minutes. The reaction was cooled to room temperature and ethyl acetate (100 mL) was added. The organic layer washed with aqueous ammonium chloride (2×50 mL) and with brine (50 mL), dried over magnesium sulfate and concentrated. The product was dissolved in dichloromethane and passed through a plug of magnesol. The solvent was removed and the clear oil obtained triturated with ether (25 mL) to give 6-(3-chloro-phenyl)-4,4-dimethyl-1,4-dihydro-3-oxa-1,8-diaza-naphthalene-2-one as a white solid (0.087 g, 80%): mp 214–215° C.; $^1$H-NMR (DMSO-d$_6$) δ10.9 (s, 1H), 8.56 (d, 1H, J=2.35 Hz), 8.06 (d, 1H, J=2.35 Hz), 7.86 (t, 1H, J=2.35 Hz), 7.72 (td, 1H, J=9.4, 2.35 Hz), 7.54–7.44 (m, 2H), 1.69 (s, 6H); MS (ESI) m/z 289 ([M+H]$^+$, 100%); Anal. Calc. For C$_{17}$H$_{17}$NO$_3$: C, 62.40; H, 4.54; N, 9.70. Found: C, 60.53; H, 4.40; N, 9.21.

EXAMPLE 5

6-Chloro-3-nitro-pyridine-2-carbonitrile

A mixture of 2,6-dichloro-3-nitropyridine and cuprous cyanide in 1-methyl-2-pyrrolidinone was quickly heated to 180° C. and maintained at that temperature for 15 minutes with vigorous stirring. The mixture was cooled to −10° C. and the deep brown solution was poured into ice water (3.5 L) and stirred for 30 min. The flocculent brown precipitate was collected and washed with H$_2$O. After drying for about 1.5 h, the moist solid was extracted with boiling toluene (3×300 mL). The combined toluene extracts were washed with H$_2$O, brine, and dried (MgSO$_4$), concentrated. The crude product was crystallized from EtOAc/hexane to afford the title compound: mp 115–117° C.; $^1$H NMR(DMSO-d$_6$) δ8.16 (dd, 1H, J=8.7, 3.0 Hz), 8.82 (d, 1H, J=9.0 Hz); MS (EI) m/z 183/185 (M+H)$^+$; Anal Calc. For C$_6$H$_2$ClN$_3$O$_2$: C, 39.26; H, 1.10; N, 22.89. Found: C, 39.47; H, 1.38; N, 22.77.

EXAMPLE 6

3-Amino-6-chloro-pyridine-2-carbonitrile

To a solution of 2,6-dichloro-3-nitropyridine(4.8 g, 26.15 mmol) in MeOH (60 mL) and concentrated HCl (25 mL) was slowly added iron powder (5.12 g, 91.53 mmol). After the completion of addition, the mixture was refluxed for 45 minutes and poured into 700 mL of H$_2$O. Filtration of the resulting slurry gave a dull yellow solid. The filtrate was made basic with concentrated NH$_4$OH, the resulting slurry was filtered and both the solid and the filtrates were extracted with ether. The combined extracts were dried (MgSO$_4$) and evaporated to give the title compound as a creamy solid (2.8 g, 58%): mp 162–165° C. which was used in next step without further purification.

EXAMPLE 7

1-(3-Amino-6-chloro-pyridin-2-yl-ethanone

To a solution of 3-amino-6-chloro-pyridine-2-carbonitrile (0.75 g, 4.88 mmol) in anhydrous THF (25 mL) under nitrogen was added a solution of methylmagnesium bromide (3M in ether, 8.1 mL, 24.3 mmol). The reaction mixture was stirred for 30 minutes and then slowly quenched with H$_2$O, and treated with 5N HCl solution. The mixture was extracted with ethyl acetate (3×100 mL) and organic extracts were washed with brine, and dried (MgSO$_4$). After removal of the solvent, the residue was purified by a chromatography using EtOAc/hexane mixture (1:3) as eluent to afford the title compound as a greenish crystalline solid: (0.71 g, 85%): mp: 108–110° C. $^1$H NMR (DMSO-d$_6$) δ2.51 (s, 3H), 7.28–7.39 ( m, 4H); MS(ESI) m/z 171/173 (M+H)$^+$; Anal. Calc. For C$_7$H$_7$ClN$_2$O: C, 49.28; H, 4.14; N, 16.14. Found: C, 49.70; H, 4.03; N, 16.41.

EXAMPLE 8

1-(3-Amino-6-chloro-pyridin-2-yl)-propan-2-ol

To a solution of 1-(3-amino-6-chloro-pyridin-2-yl)-ethanone in anhydrous THF under N$_2$ was added a solution of methylmagnesium bromide (3N in ether). The resulting reaction mixture was stirred at room temperature for 4 h, then slowly quenched with H$_2$O, treated with 0.5 N HCl and stirred for 30 minutes, diluted with ethyl acetate, washed with brine, dried (MgSO$_4$), concentrated, and chromatographed using a mixture of EtOAc/Hexane (3.5:6.5) to afford the title compound as a white crystals (0.45 g, 82%): mp: 118–121° C. $^1$H NMR(DMSO-d$_6$) δ1.45(s, 6H), 3.35(s, 1H), 5.51(s, 1H), 5.68(s, 1H), 7.02(s, 1H); MS((+)APCI) m/z 187/189 (M+H)$^+$; Anal. Calc. For C$_8$H$_{11}$ClN$_2$O: C, 51.48; H, 5.94; N, 15.01. Found: C, 51.22; H, 5.99; N, 14.47.

EXAMPLE 9

6-Chloro-4,4-dimethyl-1,4-dihydro-3-oxa-1,5-diaza-naphthalen-2-one

To a solution of 1-(3-amino-6-chloro-3-nitro-pyridin-2-yl)-propan-2-ol (0.3 g, 1.67 mmol) in anhydrous THF (20 mL) was added a solution of 1,1'-carbonyldiimidazole (0.68 g, 4.12 mmol) in anhydrous THF (10 mL). The reaction mixture was heated under reflux for 3 h. The reaction mixture was treated with 0.5N HCl, washed with brine, H$_2$O, dried (MgSO$_4$), concentrated and crystallized from EtOAc/hexane to obtain the title compound as a white crystalline solid (0.2 g, 56%): mp 175–178° C. $^1$H NMR( DMSO-d$_6$) δ1.60 (s, 6H), 7.30 (d, 1H, J=8.41 Hz), 7.41 (d, 1H, J=8.41 Hz), 10.47 (s, 1H); MS((+)APCI) m/z 213 (M+H)$^+$; Anal. Calc. For C$_9$H$_9$ClN$_2$O$_2$: C, 50.84; H, 4.27; N, 13.17. Found: C, 50.99; H, 4.28; N, 12.98.

EXAMPLE 10

The compounds of this invention were tested in the relevant assay as described below and their potency are in the range of 0.01 nM to 5 μM in the in vitro assays and 0.001 to 300 mg/kg in the in vivo assays. The selected example is example 4.

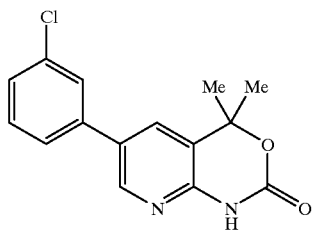

Example 4, hPR CV-1, $IC_{50}$ =0.8 μM

A. In-vitro biology

The in-vitro biology is determined by (1) competitive Radioligand Binding: using the A-form of the human progesterone receptor with progesterone as the radioligand; (2) co-transfection assay, which provides functional activity expressed as agonist EC50 and Antagonist IC50 values; (3) a T47D cell proliferation, which is a further functional assay which also provides agonist and antagonist data; and (4) T47D cell alkaline phosphatase assay, which is a further functional assay which also provides agonist and antagonist data.

1. hPR Binding assay

This assay is carried out in accordance with: Pathirana, C.; Stein, R. B.; Berger, T. S.; Fenical, W.; Ianiro, T.; Mais, D. E.; Torres, A.; Glodman, M. E., *Nonsteroidal human progesterone receptor modulators from the marine alga cymoplia barbata*, J. Steroid Biochem. Mol. Biol., 1992, 41, 733–738.

2. PRE-luciferase assay in CV-1 cells

The object of this assay is to determine a compound's progestational or antiprogestational potency based on its effect on PRE-luciferase reporter activity in CV-1 cells co-transfected with human PR and PRE-luciferase plasmids. The materials methods used in the assay are as follows.

a. Medium

The growth medium was as follows: DMEM (Bio Whittaker) containing 10% (v/v) fetal bovine serum (heat inactivated), 0.1 mM MEM non-essential amino acids, 100 U/ml penicillin, 100 mg/ml streptomycin, and 2 mM GlutaMax (GIBCO, BRL). The experimental medium was as follows: DMEM (Bio Whittaker), phenol red-free, containing 10% (v/v) charcoal-stripped fetal bovine serum (heat-inactivated), 0.1 mM MEM non-essential amino acids, 100 U/ml penicillin, 100 mg/ml streptomycin, and 2 mM GlutaMax (GIBCO, BRL).

b. Cell culture, transfection, treatment, and luciferase assay

Stock CV-1 cells are maintained in growth medium. Co-transfection is done using $1.2 \times 10^7$ cells, 5 mg pLEM plasmid with hPR-B inserted at Sphl and BamHl sites, 10 mg pGL3 plasmid with two PREs upstream of the luciferase sequence, and 50 mg sonicated calf thymus DNA as carrier DNA in 250 ml. Electroporation is carried out at 260 V and 1,000 mF in a Biorad Gene Pulser II. After electroporation, cells are resuspended in growth medium and plated in 96-well plate at 40,000 cells/well in 200 μl. Following overnight incubation, the medium is changed to experimental medium. Cells are then treated with reference or test compounds in experimental medium. Compounds are tested for antiprogestational activity in the presence of 3 nM progesterone. Twenty-four hr. after treatment, the medium is discarded, cells are washed three times with D-PBS (GIBCO, BRL). Fifty μl of cell lysis buffer (Promega, Madison, Wis.) is added to each well and the plates are shaken for 15 min in a Titer Plate Shaker (Lab Line Instrument, Inc.). Luciferase activity is measured using luciferase reagents from Promega.

c. Analysis of Results:

Each treatment consists of at least 4 replicates. Log transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear response analyses.

d. Reference Compounds

Progesterone and trimegestone are reference progestins and RU486 is the reference antiprogestin. All reference compounds are run in fill dose-response curves and the $EC_{50}$ or $IC_{50}$ values are calculated.

TABLE 1

Estimated $EC_{50}$, standard error (SE), and 95% confidence intervals (CI) for reference progestins from three individual studies

| Compound | Exp. | $EC_{50}$ (nM) | SE | 95% CI lower | 95% CI upper |
| --- | --- | --- | --- | --- | --- |
| Progesterone | 1 | 0.616 | 0.026 | 0.509 | 0.746 |
|  | 2 | 0.402 | 0.019 | 0.323 | 0.501 |
|  | 3 | 0.486 | 0.028 | 0.371 | 0.637 |
| Trimegestone | 1 | 0.0075 | 0.0002 | 0.0066 | 0.0085 |
|  | 2 | 0.0081 | 0.0003 | 0.0070 | 0.0094 |
|  | 3 | 0.0067 | 0.0003 | 0.0055 | 0.0082 |

TABLE 2

Estimated $IC_{50}$, standard error (SE), and 95% confident interval (CI) for the antiprogestin, RU486 from three individual studies

| Compound | Exp. | $IC_{50}$ (nM) | SE | 95% CI lower | 95% CI upper |
| --- | --- | --- | --- | --- | --- |
| RU486 | 1 | 0.028 | 0.002 | 0.019 | 0.042 |
|  | 2 | 0.037 | 0.002 | 0.029 | 0.048 |
|  | 3 | 0.019 | 0.001 | 0.013 | 0.027 |

Progestational activity: Compounds that increase PRE-luciferase activity significantly (p<0.05) compared to vehicle control are considered active.

Antiprogestational activity: Compounds that decrease 3 nM progesterone induced PRE-luciferase activity significantly (p<0.05)

$EC_{50}$: Concentration of a compound that gives half-maximal increase PRE-luciferase activity (default-nM) with SE.

$IC_{50}$: Concentration of a compound that gives half-maximal decrease in 3 nM progesterone induced PRE-luciferase activity (default-nM) with SE.

3. T47D cell proliferation assay

The objective of this assay is the determination of progestational and antiprogestational potency by using a cell proliferation assay in T47D cells. A compound's effect on DNA synthesis in T47D cells is measured. The materials and methods used in this assay are as follows.

a. Growth medium

DMEM:F12 (1:1) (GIBCO, BRL) supplemented with 10% (v/v) fetal bovine serum (not heat-inactivated), 100 U/ml penicillin, 100mg/ml streptomycin, and 2 mM GlutaMax (GIBCO, BRL).

b. Treatment medium

Minimum Essential Medium (MEM) (#51200-038GIBCO, BRL) phenol red-free supplemented with 0.5% charcoal stripped fetal bovine serum, 100 U/ml penicillin, 200 mg/ml streptomycin, and 2 mM GlutaMax (GIBCO, BRL).

c. Cell culture

Stock T47 D cells are maintained in growth medium. For BrdU incorporation assay, cells are plated in 96-well plates (Falcon, Becton Dickinson Labware) at 10,000 cells/well in growth medium. After overnight incubation, the medium is changed to treatment medium and cells are cultured for an additional 24 hr before treatment. Stock compounds are dissolved in appropriate vehicle (100% ethanol or 50% ethanol/50% DMSO), subsequently diluted in treatment medium and added to the cells. Progestin and antiprogestin reference compounds are run in fill dose-response curves. The final concentration of vehicle is 0.1%. In control wells, cells receive vehicle only. Antiprogestins are tested in the presence of 0.03 nM trimegestone, the reference progestin agonist. Twenty-four hours after treatment, the medium is discarded and cells are labeled with 10 mM BrdU (Amersham Life Science, Arlington Heights, Ill.) in treatment medium for 4 hr.

d. Cell Proliferation Assay

At the end of BrdU labeling, the medium is removed and BrdU incorporation is measured using a cell proliferation ELISA kit (#RPN 250, Amersham Life Science) according to manufacturer's instructions. Briefly, cells are fixed in an ethanol containing fixative for 30 min followed by incubation in a blocking buffer for 30 min to reduce background. Peroxidase-labeled anti-BrdU antibody is added to the wells and incubated for 60 min. The cells are rinsed three times with PBS and incubated with 3,3'5,5'-tetramethylbenzidine (TMB) substrate for 10–20 min depending upon the potency of tested compounds. Then 25 µl of 1 M sulfuric acid is added to each well to stop color reaction and optical density is read in a plate reader at 450 nm within 5 min.

e. Analysis of Results

Square root-transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear dose response analyses in both single dose and dose response studies.

f. Reference Compounds

Trimegestone and medroxyprogesterone acetate (MPA) are reference progestins and RU486 is the reference antiprogestin. All reference compounds are run in full dose-response curves and the $EC_{50}$ or $IC_{50}$ values are calculated.

TABLE 3

Estimated $EC_{50}$, standard error (SE), and 95% confidence intervals (CI) for individual studies

| Compound | Exp | $EC_{50}$ (nM) | SE | 95% CI lower | 95% CI upper |
|---|---|---|---|---|---|
| Trimegestone | 1 | 0.017 | 0.003 | 0.007 | 0.040 |
|  | 2 | 0.014 | 0.001 | 0.011 | 0.017 |
|  | 3 | 0.019 | 0.001 | 0.016 | 0.024 |
| MPA | 1 | 0.019 | 0.001 | 0.013 | 0.027 |
|  | 2 | 0.017 | 0.001 | 0.011 | 0.024 |

TABLE 4

Estimated $IC_{50}$, standard error, and 95% confident interval for the antiprogestin, RU486

| Compound | Exp | $IC_{50}$ (nM) | SE | 95% CI lower | 95% CI upper |
|---|---|---|---|---|---|
| RU486 | 1 | 0.011 | 0.001 | 0.008 | 0.014 |
|  | 2 | 0.016 | 0.001 | 0.014 | 0.020 |
|  | 3 | 0.018 | 0.001 | 0.014 | 0.022 |

$EC_{50}$: Concentration of a compound that gives half-maximal increase in BrdU incorporation with SE; $IC_{50}$: Concentration of a compound that gives half-maximal decrease in 0.1 trimegestone induced BrdU incorporation with SE 4. T47D cell alkaline phosphatase assay The purpose of this assay is to identify progestins or antiprogestins by determining a compound's effect on alkaline phosphatase activity in T47D cells. The materials and methods used in this assay are as follows.

a. Culture medium

DMEM:F12(1:1)(GIBCO, BRL) supplemented with 5% (v/v) charcoal stripped fetal bovine serum (not heat-inactivated), 100 U/ml penicillin, 100 µg/ml streptomycin, and 2 mM GlutaMax (GIBCO, BRL).

b. Alkaline phosphatase assay buffer

I. 0.1 M Tris-HCl, pH 9.8, containing 0.2% Triton X-100

II. 0.1 M Tris-HCl, pH 9.8 containing 4 mM p-nitrophenyl phosphate (Sigma).

C. Cell Culture and Treatment

Frozen T47D cells were thawed in a 37° C. water bath and diluted to 280,000 cells/ml in culture medium. To each well in a 96-well plate (Falcon, Becton Dickinson Labware), 180 µl of diluted cell suspension was added. Twenty µl of reference or test compounds diluted in the culture medium was then added to each well. When testing for progestin antagonist activity, reference antiprogestins or test compounds were added in the presence of 1 nM progesterone. The cells were incubated at 37° C. in a 5% $CO_2$/humidified atmosphere for 24 hr.

d. Alkaline Phosphatase Enzyme Assay

At the end of treatment, the medium was removed from the plate and fifty µl of assay buffer I was added to each well. The plates were shaken in a titer plate shaker for 15 min. Then 150 µl of assay buffer II was added to each well. Optical density measurements were taken at 5 min intervals for 30 min at a test wavelength of 405 nM.

e. Analysis of Results: Analysis of dose-response data

For reference and test compounds, a dose response curve is generated for dose (X-axis) vs. the rate of enzyme reaction (slope) (Y-axis). Square root-transformed data are used for analysis of variance and nonlinear dose response curve fitting for both agonist and antagonist modes. Huber weighting is used to downweight the effects of outliers. $EC_{50}$ or $IC_{50}$ values are calculated from the retransformed values. JMP software (SAS Institute, Inc.) is used for both one-way analysis of variance and non-linear dose response analyses in both single dose and dose response studies.

f. Reference Compounds

Progesterone and trimegestone are reference progestins and RU486 is the reference antiprogestin. All reference compounds are run in fill dose response curves and the $EC_{50}$ or $IC_{50}$ values are calculated.

TABLE 5

Estimated $EC_{50}$, standard error (SE), and 95% confidence intervals (CI) for reference progestins from three independent experiments

| | | $EC_{50}$ | | 95% CI | |
|---|---|---|---|---|---|
| Compound | Exp. | (nM) | SE | lower | upper |
| Progesterone | 1 | 0.839 | 0.030 | 0.706 | 0.996 |
| | 2 | 0.639 | 0.006 | 0.611 | 0.669 |
| | 3 | 1.286 | 0.029 | 1.158 | 1.429 |
| Trimegestone | 1 | 0.084 | 0.002 | 0.076 | 0.091 |
| | 2 | 0.076 | 0.001 | 0.072 | 0.080 |
| | 3 | 0.160 | 0.004 | 0.141 | 0.181 |

TABLE 6

Estimated $IC_{50}$, standard error, and 95% confident interval for the reference antiprogestin RU486 from three independent experiments

| | | $IC_{50}$ | | 95% CI | |
|---|---|---|---|---|---|
| Compound | Exp | (nM) | SE | lower | upper |
| RU486 | 1 | 0.103 | 0.002 | 0.092 | 0.115 |
| | 2 | 0.120 | 0.001 | 0.115 | 0.126 |
| | 3 | 0.094 | 0.007 | 0.066 | 0.134 |

B. In-vivo Biology

The primary in-vivo assay is the rat decidualization model, which may be used to determine progestational effects of both agonists and antagonists. The secondary in-vivo assay is the rat ovulation inhibition model, which is under development, and hence the protocol is un-available.

1. Rat decidualization assay

The objective of this procedure is used to evaluate the effect of progestins and antiprogestins on rat uterine decidualization and compare the relative potencies of various test compounds. The materials and methods used in this assay are as follows.

a. Methods

Test compounds are dissolved in 100% ethanol and mixed with corn oil (vehicle). Stock solutions of the test compounds in oil (Mazola™) are then prepared by heating (~80° C.) the mixture to evaporate ethanol. Test compounds are subsequently diluted with 100% corn oil or 10% ethanol in corn oil prior to the treatment of animals. No difference in decidual response was found when these two vehicles were compared.

b. Animals (RACUC protocol #5002)

Ovariectomized mature female Sprague-Dawley rats (~60-day old and 230 g) are obtained from Taconic (Taconic Farms, N.Y.) following surgery. Ovariectomy is performed at least 10 days prior to treatment to reduce circulating sex steroids. Animals are housed under 12 hr light/dark cycle and given standard rat chow and water ad libitum.

c. Treatment

Rats are weighed and randomly assigned to groups of 4 or 5 before treatment. Test compounds in 0.2 ml vehicle are administered by subcutaneous injection in the nape of the neck or by gavage using 0.5 ml. The animals are treated once daily for seven days. For testing antiprogestins, animals are given the test compounds and a $EC_{50}$ dose of progesterone (5.6 mg/kg) during the first three days of treatment. Following decidual stimulation, animals continue to receive progesterone until necropsy four days later.

d. Dosing

Doses are prepared based upon mg/kg mean group body weight. In all studies, a control group receiving vehicle is included. Determination of dose-response curves is carried out using doses with half log increases (e.g. 0.1, 0.3, 1.0, 3.0 mg/kg . . . ).

e. Decidual induction

Approximately 24 hr after the third injection, decidualization is induced in one of the uterine horns by scratching the antimesometrial luminal epithelium with a blunt 21 G needle. The contralateral horn is not scratched and serves as an unstimulated control. Approximately 24 hr following the final treatment, rats are sacrificed by $CO_2$ asphyxiation and body weight measured. Uteri are removed and trimmed of fat. Decidualized (D-horn) and control (C-horn) uterine horns are weighed separately.

f. Analysis of Results

The increase in weight of the decidualized uterine horn is calculated by D-horn/C-horn and logarithmic transformation is used to maximize normality and homogeneity of variance. The Huber M-estimator is used to down weight the outlying transformed observations for both dose-response curve fitting and one-way analysis of variance. JMP software (SAS Institute, Inc.) is used for both one-way ANOVA and non-linear dose-response analyses.

g. Reference Compounds

All progestin reference compounds were run in full dose-response curves and the $EC_{50}$ for uterine wet weight were calculated.

TABLE 7

Estimated $EC_{50}$, standard error (SE), and 95% confidence intervals for individual studies

| | | $EC_{50}$ | | 95% CI | |
|---|---|---|---|---|---|
| Compound | Exp | (mg/kg, s.c.) | SE | lower | upper |
| Progesterone | 1 | 5.50 | 0.77 | 4.21 | 7.20 |
| | 2 | 6.21 | 1.12 | 4.41 | 8.76 |
| 3-Ketodesogestrel | 1 | 0.11 | 0.02 | 0.07 | 0.16 |
| | 2 | 0.10 | 0.05 | 0.11 | 0.25 |
| | 3 | 0.06 | 0.03 | 0.03 | 0.14 |
| Levonorgestrel | 1 | 0.08 | 0.03 | 0.04 | 0.16 |
| | 2 | 0.12 | 0.02 | 0.09 | 0.17 |
| | 3 | 0.09 | 0.02 | 0.06 | 0.13 |
| | 4 | 0.09 | 0.02 | 0.06 | 0.14 |
| MPA | 1 | 0.42 | 0.03 | 0.29 | 0.60 |
| | 2 | 0.39 | 0.05 | 0.22 | 0.67 |
| | 3 | 0.39 | 0.04 | 0.25 | 0.61 |

TABLE 8

Estimated average $EC_{50}$, standard error, and 95% confidence intervals for dose-response curves of 3 reference compounds

| | $EC_{50}$ | | 95% CI | |
|---|---|---|---|---|
| Compound | (mg/kg, s.c.) | SE | lower | upper |
| Progesterone | 5.62 | 0.62 | 4.55 | 7.00 |
| 3-Ketodesogestrel | 0.10 | 0.02 | 0.07 | 0.14 |
| Levonorgestrel | 0.10 | 0.01 | 0.08 | 0.12 |

TABLE 9

Estimated IC$_{50}$, standard error, and 95% confident interval for the antiprogestin, RU 486

| Compound | Exp. | IC$_{50}$ (mg/kg p.o.) | SE | 95% CI lower | 95% CI upper |
|---|---|---|---|---|---|
| RU 486 | 1 | 0.21 | 0.07 | 0.05 | 0.96 |
|  | 2 | 0.14 | 0.02 | 0.08 | 0.27 |

Concentration: Compound concentration in assay (default-mg/kg body weight)
Route of administration: Route the compound is administered to the animals
Body weight: Mean total animal body weight (default-kg)
D-horn: Wet weight of decidualized uterine horn (default-mg)
C-horn: Wet weight of control uterine horn (default-mg)
Decidual response: [(D-C)/C]×400%
Progestational activity: Compounds that induce decidualization significantly (p<0.05) compared to vehicle control are considered active
Antiprogestational activity. Compounds that decrease EC$_{50}$ progesterone induced decidualization significantly (p<0.05)
EC$_{50}$ for uterine weight: Concentration of compound that gives half-maximal increase in decidual response (default-mg/kg)
IC$_{50}$ for uterine weight: Concentration of compound that gives half-maximal decrease in EC$_{50}$ progesterone induced decidual response (default-mg/kg)

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A compound of the formula:

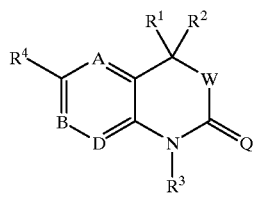

I wherein:
A, B and D are N or CH, with the proviso that one of A, B and D is N;
Q is O or S;
$R^1$ and $R^2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, COR$^A$, and NR$^B$COR$^A$;
$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^B$ is H, $C_1$ to $C_3$ alkyl, or substituted $C_1$ to $C_3$ alkyl;
$R^3$ is H, OH, NH$_2$, $C_1$ to $C_6$ alkyl, substituted $C_1$ to $C_6$ alkyl, $C_3$ to $C_6$ alkenyl, substituted $C_3$ to $C_6$ alkenyl, or COR$^C$;
$R^C$ is H, $C_1$ to $C_3$ alkyl, substituted $C_1$ to $C_3$ alkyl, aryl, substituted aryl, $C_1$ to $C_4$ alkoxy, substituted $C_1$ to $C_4$ alkoxy, $C_1$ to $C_4$ aminoalkyl, or substituted $C_1$ to $C_4$ aminoalkyl;
$R^4$ is selected from the group consisting of a), b), c), and d):
a) a trisubstituted benzene ring having the substituents X, Y and Z and having the structure shown below:

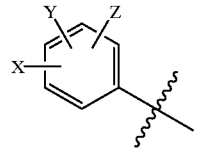

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, NO$_2$, $C_1$ to $C_3$ perfluoroalkyl, 5 or 6 membered heterocyclic ring having in its backbone 1 to 3 heteroatoms, COR$^D$, OCOR$^D$, and NR$^E$COR$^D$;
$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^E$ is H, $C_1$ to $C_3$ alkyl, or substituted $C_1$ to $C_3$ alkyl;
Y and Z are independent substituents selected from the group consisting of halogen, CN, NO$_2$, $C_1$ to $C_3$ alkoxy, $C_1$ to $C_3$ alkyl, and $C_1$ to $C_3$ thioalkoxy;
b) a mono-substituted or disubstituted benzene ring having the substituents X, Y and Z and of the structure as shown below:

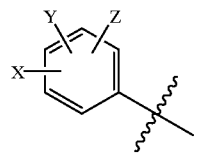

X is selected from the group consisting of $C_1$ to $C_3$ thioalkoxy, substituted $C_1$ to $C_3$ thioalkoxy, NO$_2$, $C_1$ to $C_3$ perfluoroalkyl, 5 or 6 membered heterocyclic ring having in its backbone 1 to 3 heteroatoms, COR$^{D'}$, OCOR$^{D'}$, and NR$^E$COR$^{D'}$;
$R^{D'}$ is selected from the group consisting of H, $C_2$ to $C_3$ alkyl, substituted $C_2$ to $C_3$ alkyl, aryl, substituted aryl, $C_1$ to $C_3$ alkoxy, substituted $C_1$ to $C_3$ alkoxy, $C_1$ to $C_3$ aminoalkyl, and substituted $C_1$ to $C_3$ aminoalkyl;
Y and Z are independent substituents selected from the group consisting of H, NO$_2$, and $C_1$ to $C_3$ thioalkoxy;
wherein at least one of Y or Z is H;
c) a five or six membered ring having in its backbone 1, 2, or 3 heteroatoms selected from the group consisting of SO and SO$_2$ and having one or two independent substituents selected from the group consisting of H, halogen, CN, NO$_2$, C$_1$ to C$_3$ alkyl, C$_1$ to C$_3$ alkoxy, C$_1$ to C$_3$ aminoalkyl, COR$^F$, and NR$^G$COR$^F$;

R$^F$ is H, C$_1$ to C$_3$ alkyl, substituted C$_1$ to C$_3$ alkyl, aryl, substituted aryl, C$_1$ to C$_3$ alkoxy, substituted C$_1$ to C$_3$ alkoxy, C$_1$ to C$_3$ aminoalkyl, or substituted C$_1$ to C$_3$ aminoalkyl;

R$^G$ is H, C$_1$ to C$_3$ alkyl, or substituted C$_1$ to C$_3$ alkyl; and d) a five or six membered ring having in its backbone 1, 2, or 3 heteroatoms selected from the group consisting of O and S and having one or two independent substituents selected from the group consisting of NO$_2$, COR$^F$, and NR$^G$COR$^F$;

wherein if said ring is substituted with one NO$_2$, COR$^F$, or NR$^G$COR$^F$ substituent, said second substituent may be selected from the group consisting of halogen, CN, NO$_2$, C$_1$ to C$_3$ alkyl, C$_1$ to C$_3$ alkoxy, C$_1$ to C$_3$ aminoalkyl, COR$^F$, and NR$^G$COR$^F$;

R$^{F'}$ is C$_2$ to C$_3$ alkyl, substituted C$_2$ to C$_3$ alkyl, aryl, substituted aryl, C$_1$ to C$_3$ alkoxy, substituted C$_1$ to C$_3$ alkoxy, C$_1$ to C$_3$ aminoalkyl, or substituted C$_1$ to C$_3$ aminoalkyl;

W is O;

or a pharmaceutically acceptable salt thereof.

2. The compound according to claim 1 wherein:

R$^C$ is H, C$_1$ to C$_4$ alkyl, substituted C$_1$ to C$_4$ alkyl, aryl, substituted aryl, C$_1$ to C$_3$ alkoxy, substituted C$_1$ to C$_3$ alkoxy, C$_1$ to C$_3$ aminoalkyl, or substituted C$_1$ to C$_3$ aminoalkyl;

wherein R$^4$ is (i), (ii), or (iii):
(i) the trisubstituted benzene ring a), wherein:
X is selected from the group consisting of halogen, CN, C$_1$ to C$_3$ alkyl, substituted C$_1$ to C$_3$ alkyl, C$_1$ to C$_3$ alkoxy, substituted C$_1$ to C$_3$ alkoxy, C$_1$ to C$_3$ thioalkoxy, substituted C$_1$ to C$_3$ thioalkoxy, C$_1$ to C$_3$ aminoalkyl, substituted C$_1$ to C$_3$ aminoalkyl, NO$_2$, C$_1$ to C$_3$ perfluoroalkyl, a 5 membered heterocyclic ring having in its backbone 1 to 3 heteroatoms, COR$^D$, OCOR$^D$, and NR$^E$COR$^D$;

(ii) the mono-substituted or disubstituted benzene ring b), wherein:
X is selected from the group consisting of C$_1$ to C$_3$ thioalkoxy, substituted C$_1$ to C$_3$ thioalkoxy, NO$_2$, C$_1$ to C$_3$ perfluoroalkyl, 5 membered heterocyclic ring having in its backbone 1 to 3 heteroatoms, COR$^D$, OCOR$^D$, and NR$^E$COR$^D$ Y and Z are independent substituents selected from the group consisting of H, NO$_2$, and C$_1$ to C$_3$ thioalkoxy;
wherein at least one of Y or Z is H;
or (iii) the five or six membered ring c) or d), wherein:
said substituents are selected from the group consisting of H, halogen, CN, NO$_2$, C$_1$ to C$_3$ alkyl, and C$_1$ to C$_3$ alkoxy.

3. The compound according to claim 1 wherein:

R$^1$=R$^2$ and are selected from the group consisting of C$_1$ to C$_3$ alkyl and substituted C$_1$ to C$_3$ alkyl;

R$^3$ is H, OH, NH$_2$, C$_1$ to C$_6$ alkyl, substituted C$_1$ to C$_6$ alkyl, or COR$^C$;

R$^C$ is H, C$_1$ to C$_4$ alkyl, or C$_1$ to C$_4$ alkoxy;

R$^4$ is selected from the group consisting of (i) and (ii):
(i) the disubstituted benzene ring b) of the structure:

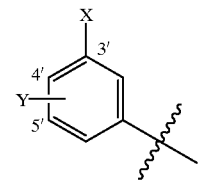

wherein:
Z is H;
X is selected from the group consisting of NO$_2$, C$_1$ to C$_3$ perfluoroalkyl, 5 membered heterocyclic ring having in its backbone 1 to 3 heteroatoms, and C$_1$ to C$_3$ thioalkoxy; and
Y is on the 4' or 5' position and is selected from the group consisting of NO$_2$ and C$_1$ to C$_3$ thioalkoxy; and (ii) the five membered ring d) of the structure:

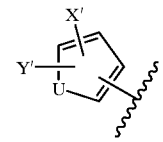

wherein:
U is O or S;
X' is NO$_2$;
Y' is selected from the group consisting of H and C$_1$ to C$_4$ alkyl.

4. The compound according to claim 3 wherein:

R$^1$=R$^2$ and are selected from the group consisting of CH$_3$ and the 6-membered saturated C-based spirocyclic ring constructed by fusing R$^1$ and R$^2$;

R$^3$ is H, OH, NH$_2$, CH$_3$, substituted methyl, or COR$^C$;

R$^C$ is H, C$_1$ to C$_3$ alkyl, or C$_1$ to C$_4$ alkoxy;

R$^4$ is the monosubstituted benzene ring (ii) having the structure as shown below:

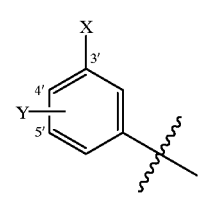

wherein:

Y and Z are H;

X is NO$_2$.

5. The compound according to claim 4 wherein $R^4$ is the moiety:

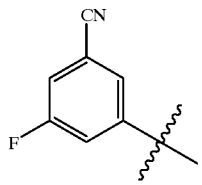

or a pharmaceutically acceptable salt thereof.

6. The compound according to claim 1 wherein:
$R^1=R^2$ and are selected from the group consisting of $CH_3$ and the 6-membered saturated C-based spirocyclic ring constructed by fusing $R^1$ and $R^2$;
$R^3$ is H, OH, $NH_2$, $CH_3$, substituted methyl, or $COR^C$;
$R^C$ is H, $C_1$ to $C_3$ alkyl, or $C_1$ to $C_4$ alkoxy;
$R^4$ is the five membered ring (iv) having the structure:

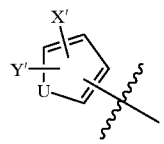

U is O or S;
X' is $NO_2$;
Y' is $C_1$ to $C_4$ alkyl.

7. The compound according to claim 4 wherein $R^4$ is:

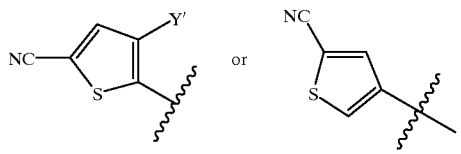

and Y' is H or $C_1$ to $C_4$ alkyl.

8. A method of inducing contraception in a mammal, the method comprising administering to a mammal in need thereof a pharmaceutically effective amount of 6-(3-Chlorophenyl)-4,4-dimethyl-1,4-dihydro-3-oxa-1,8-diaza-naphthalene-2-one or a pharmaceutically acceptable salt thereof in a pharmaceutically acceptable carrier.

9. A pharmaceutical composition comprising a pharmaceutically effective amount of a compound according to claim 1 and a pharmaceutically effective carrier or excipient.

10. A method of inducing contraception in a mammal, the method comprising administering to a mammal in need thereof a pharmaceutically effective amount of a compound according to claim 1.

11. A method of treatment of benign or malignant neoplastic disease in a mammal, the method comprising administering to a mammal in need thereof a compound according to claim 1.

12. The method according to claim 11 wherein the benign or malignant neoplastic disease is selected from the group consisting of uterine myometrial fibroids, endometriosis, benign prostatic hypertrophy; carcinomas or adenocarcinomas of the endometrium, ovary, breast, colon, prostate, pituitary, meningioma and other hormone-dependent tumors.

13. A method of treatment in a mammal of carcinomas or adenocarcinomas of the endometrium, ovary, breast, colon, or prostate, the method comprising administering to a mammal in need thereof a compound according to claim 1.

14. A compound having the formula:

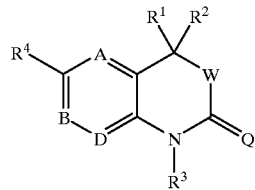

I wherein:
A, B and D are N or CH, with the proviso that one of A, B, and D is N;
Q is $NR^6$ or $CR^7R^8$;
$R^1$ and $R^2$ are independent substituents selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_2$ to $C_6$ alkynyl, substituted $C_2$ to $C_6$ alkynyl, $C_3$ to $C_8$ cycloalkyl, substituted $C_3$ to $C_8$ cycloalkyl, aryl, substituted aryl, heterocyclic, substituted heterocyclic, $COR^A$, and $NR^BCOR^A$;
$R^A$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^B$ is H, $C_1$ to $C_3$ alkyl, or substituted $C_1$ to $C_3$ alkyl;
$R^3$ is H, OH, $NH_2$, $C_1$ to $C_6$ alkyl, substituted $C_1$ to $C_6$ alkyl, $C_3$ to $C_6$ alkenyl, substituted $C_3$ to $C_6$ alkenyl, or $COR^C$;
$R^C$ is H, $C_1$ to $C_3$ alkyl, substituted $C_1$ to $C_3$ alkyl, aryl, substituted aryl, $C_1$ to $C_4$ alkoxy, substituted $C_1$ to $C_4$ alkoxy, $C_1$ to $C_4$ aminoalkyl, or substituted $C_1$ to $C_4$ aminoalkyl;
$R^4$ is a) or b):
  a) a substituted benzene ring having the substituents X, Y and Z as shown below:

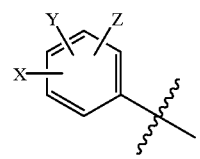

X is selected from the group consisting of halogen, CN, $C_1$ to $C_3$ alkyl, substituted $C_1$ to $C_3$ alkyl, $C_1$ to $C_4$ alkoxy, substituted $C_1$ to $C_4$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring having in its backbone 1 to 3 heteroatoms, $COR^D$, $OCOR^D$, and $NR^ECOR^D$;
$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^E$ is H, $C_1$ to $C_3$ alkyl, or substituted $C_1$ to $C_3$ alkyl;
Y and Z are independent substituents selected from the group consisting of H, halogen, CN, $NO_2$, $C_1$ to $C_3$ alkoxy, $C_1$ to $C_4$ alkyl, and $C_1$ to $C_3$ thioalkoxy;
or
b) a five or six membered ring having in its backbone 1, 2, or 3 heteroatoms selected from the group consisting of O, S, SO, $SO_2$ and $NR^5$ and having one or two independent substituents selected from the group consisting of H, halogen, CN, $NO_2$, $C_1$ to $C_3$ alkyl, $C_1$ to $C_3$ alkoxy, $C_1$ to $C_3$ aminoalkyl, $COR^F$, and $NR^G COR^F$;

$R^F$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^G$ is H, $C_1$ to $C_3$ alkyl, or substituted $C_1$ to $C_3$ alkyl;

$R^5$ is H, $C_1$ to $C_3$ alkyl, or $C_1$ to $C_4$ $CO_2$ alkyl;

$R_6$ is selected from the group consisting of CN, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, and $SO_2CF_3$;

$R^7$ and $R^8$ are independent substituents selected from the group consisting of H, $C_1$ to $C_6$ alkyl, substituted $C_1$ to $C_6$ alkyl, $C_3$ to $C_8$ cycloalkyl, substituted $C_3$ to $C_8$ cycloalkyl, aryl, substituted aryl, heterocyclic, substituted heterocyclic, $NO_2$, CN, and $CO_2R^9$;

$R^9$ is $C_1$ to $C_3$ alkyl;

or $CR^7R^8$ form a six membered ring of the structure below:

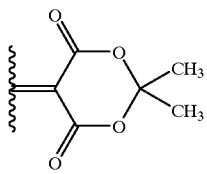

W is O;

or a pharmaceutically acceptable salt thereof.

15. The compound according to claim 14 wherein:

$R^1=R^2$ and are selected from the group consisting of $C_1$ to $C_3$ alkyl and substituted $C_1$ to $C_3$ alkyl;

$R^3$ is H, OH, $NH_2$, $C_1$ to $C_6$ alkyl, substituted $C_1$ to $C_6$ alkyl, or $COR^C$;

$R^C$ is H, $C_1$ to $C_4$ alkyl, or $C_1$ to $C_4$ alkoxy;

$R^4$ is selected from the group consisting of (i), (ii) and (iii):

(i) the substituted benzene ring a) of the structure:

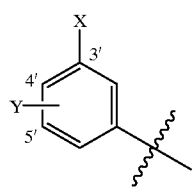

wherein:

Z is H;

X is selected from the group consisting of halogen, CN, $C_1$ to $C_3$ alkoxy, $C_1$ to $C_3$ alkyl, $NO_2$, $C_1$ to $C_8$ perfluoroalkyl, 5 membered heterocyclic ring having in its backbone 1 to 3 heteroatoms, and $C_1$ to $C_3$ thioalkoxy; and Y is on the 4' or 5' position and is selected from the group consisting of H, halogen, CN, $NO_2$, $C_1$ to $C_3$ alkoxy, $C_1$ to $C_4$ alkyl, and $C_1$ to $C_3$ thioalkoxy;

(ii) the five membered ring b) of the structure:

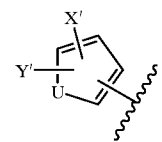

wherein:

U is O, S, or $NR^5$;

$R^5$ is H, $C_1$ to $C_3$ alkyl, or $C_1$ to $C_4$ $CO_2$ alkyl;

X' is selected from the group consisting of halogen, CN, $NO_2$, $C_1$ to $C_3$ alkyl, and $C_1$ to $C_3$ alkoxy;

Y' is selected from the group consisting of H and $C_1$ to $C_4$ alkyl; and (iii) the six membered ring b) of the structure:

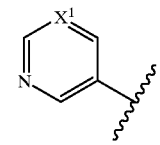

$X^1$ is N or $CX^2$;

$X^2$ is halogen, CN, or $NO_2$.

16. The compound according to claim 14 wherein:

$R^1=R^2$ and are;

$R^3$ is H, OH, $NH_2$, $C_1$ alkyl, substituted $C_1$ alkyl, or $COR^C$;

$R^C$ is H, $C_1$ to $C_3$ alkyl, or $C_1$ to $C_4$ alkoxy;

$R^4$ is the substituted benzene ring a) of the structure:

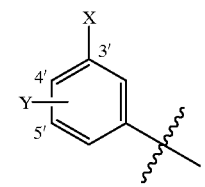

X is halogen or CN;

Y is on the 4' or 5' position and is selected from the group consisting of H and halogen;

wherein said halogen is F.

17. The compound according to claim 14 wherein:

$R^1=R^2$ and are $CH_3$;

$R^4$ is the five membered ring b) of the structure:

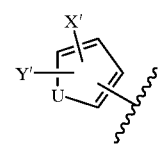

U is O, S, or NH;

X' is halogen, CN, or $NO_2$;

Y' is H or $C_1$ to $C_4$ alkyl.

18. The compound according to claim 14, wherein:

$R^4$ is (i) or (ii):

(i) the substituted benzene ring a), wherein:

X is selected from the group consisting of halogen, CN, $C_1$ to $C_3$ alkyl, substituted $C_1$ to $C_3$ alkyl, $C_1$ to $C_3$ alkoxy, substituted $C_1$ to $C_3$ alkoxy, $C_1$ to $C_3$ thioalkoxy, substituted $C_1$ to $C_3$ thioalkoxy, $C_1$ to $C_3$ aminoalkyl, substituted $C_1$ to $C_3$ aminoalkyl, $NO_2$, $C_1$ to $C_3$ perfluoroalkyl, a 5 membered heterocyclic ring having in its backbone 1 to 3 heteroatoms, $COR^D$, $OCOR^D$, and $NR^E COR^D$;

or (ii) the five or six membered ring b) having in its backbone 1, 2, or 3 heteroatoms selected from the group consisting of O, S, SO, $SO_2$ and $NR^5$, said ring having one or two independent substituents selected from the group consisting of H, halogen, CN, $NO_2$, $C_1$ to $C_3$ alkyl, and $C_1$ to $C_3$ alkoxy.

19. A method of treatment in a mammal of carcinomas or adenocarcinomas of the endometrium, ovary, breast, colon, or prostate, the method comprising administering to a mammal in need thereof a compound according to claim 14.

20. A pharmaceutical composition comprising a pharmaceutically effective amount of a compound according to claim 14 and a pharmaceutically effective carrier or excipient.

21. A method of inducing contraception in a mammal, the method comprising administering to a mammal in need thereof a pharmaceutically effective amount of a compound according to claim 14.

22. A compound of the formula:

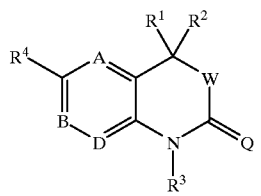

I wherein:

A, B and D are N or CH, with the proviso that one of A, B, and D is N;

Q is O, S, $NR^6$, or $CR^7R^8$;

$R^1$ is $C_1$ to $C_6$ alkyl;

$R^2$ is selected from the group consisting of H, $C_1$ to $C_6$ alkyl, substituted $C_1$ to $C_6$ alkyl, $C_2$ to $C_6$ alkenyl, substituted $C_2$ to $C_6$ alkenyl, $C_3$ to $C_8$ cycloalkyl, substituted $C_3$ to $C_8$ cycloalkyl, aryl, substituted aryl, heterocyclic, substituted heterocyclic, $COR^A$, and $NR^B COR^A$;

$R^3$ is H, OH, $NH_2$, $C_1$ to $C_6$ alkyl, substituted $C_1$ to $C_6$ alkyl, $C_3$ to $C_6$ alkenyl, substituted $C_3$ to $C_6$ alkenyl, or $COR^C$;

$R^C$ is H, $C_1$ to $C_3$ alkyl, substituted $C_1$ to $C_3$ alkyl, aryl, substituted aryl, $C_1$ to $C_4$ alkoxy, substituted $C_1$ to $C_4$ alkoxy, $C_1$ to $C_4$ aminoalkyl, or substituted $C_1$ to $C_4$ aminoalkyl;

$R^4$ is selected from the group consisting of a), b), and c):

a) a substituted benzene ring having the substituents X, Y and Z as shown below:

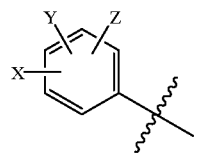

wherein:

X is selected from the group consisting of halogen, CN, $C_1$ to $C_3$ alkyl, substituted $C_1$ to $C_3$ alkyl, $C_1$ to $C_4$ alkoxy, substituted $C_1$ to $C_4$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring having in its backbone 1 to 3 heteroatoms, $COR^D$, $OCOR^D$, and $NR^E COR^D$;

$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^E$ is H, $C_1$ to $C_3$ alkyl, or substituted $C_1$ to $C_3$ alkyl;

Y and Z are independent substituents selected from the group consisting of H, halogen, CN, $NO_2$, $C_1$ to $C_3$ alkoxy, $C_1$ to $C_4$ alkyl, and $C_1$ to $C_3$ thioalkoxy;

b) a five membered ring having in its backbone 1, 2, or 3 heteroatoms selected from the group consisting of O, S, SO, $SO_2$ and $NR^5$ and having one or two independent substituents selected from the group consisting of H, halogen, CN, $NO_2$, $C_1$ to $C_3$ alkyl, $C_1$ to $C_3$ alkoxy, $C_1$ to $C_3$ aminoalkyl, $COR^F$, and $NR^G COR^F$; and c) a six membered ring having in its backbone 2 or 3 heteroatoms selected from the group consisting of O, S, SO, $SO_2$ and $NR^5$ and having one or two independent substituents selected from the group consisting of H, halogen, CN, $NO_2$, $C_1$ to $C_3$ alkyl, $C_1$ to $C_3$ alkoxy, $C_1$ to $C_3$ aminoalkyl, $COR^F$, and $NR^G COR^F$;

$R^F$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;

$R^G$ is H, $C_1$ to $C_3$ alkyl, or substituted $C_1$ to $C_3$ alkyl;

$R^5$ is H, $C_1$ to $C_3$ alkyl, or $C_1$ to $C_4$ $CO_2$ alkyl;

W is O;

or a pharmaceutically acceptable salt thereof.

23. The compound according to claim 22, wherein:

$R^1=R^2$ and are $C_1$ to $C_3$ alkyl;

$R^3$ is H, OH, $NH_2$, $C_1$ to $C_6$ alkyl, substituted $C_1$ to $C_6$ alkyl, or $COR^C$;

$R^C$ is H, $C_1$ to $C_4$ alkyl, or $C_1$ to $C_4$ alkoxy;

$R^4$ is selected from the group consisting of (i), (ii) and (iii):

(i) the substituted benzene ring a) of the structure:

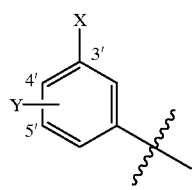

wherein:
Z is H;
X is selected from the group consisting of halogen, CN, $C_1$ to $C_3$ alkoxy, $C_1$ to $C_3$ alkyl, $NO_2$, $C_1$ to $C_3$ perfluoroalkyl, 5 membered heterocyclic ring having in its backbone 1 to 3 heteroatoms, and $C_1$ to $C_3$ thioalkoxy; and
Y is on the 4' or 5' position and is selected from the group consisting of H, halogen, CN, $NO_2$, $C_1$ to $C_3$ alkoxy, $C_1$ to $C_4$ alkyl, and $C_1$ to $C_3$ thioalkoxy;
(ii) the five membered ring b) of the structure:

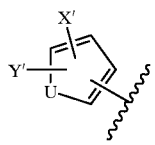

wherein:
U is O, S, or $NR^5$;
$R^5$ is H, $C_1$ to $C_3$ alkyl, or $C_1$ to $C_4$ $CO_2$ alkyl;
X' is selected from the group consisting of halogen, CN, $NO_2$, $C_1$ to $C_3$ alkyl, and $C_1$ to $C_3$ alkoxy;
Y' is selected from the group consisting of H and $C_1$ to $C_4$ alkyl;
(iii) the six membered ring c) of the structure:

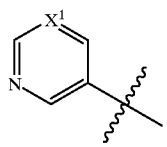

$X^1$ is N.
24. The compound according to claim 22 wherein:
$R^1=R^2$ and are $CH_3$;
$R^3$ is H, OH, $NH_2$, $C_1$ alkyl, substituted $C_1$ alkyl, or $COR^C$;
$R^C$ is H, $C_1$ to $C_3$ alkyl, or $C_1$ to $C_4$ alkoxy;
$R^4$ is the substituted benzene ring a) of the structure as shown below:

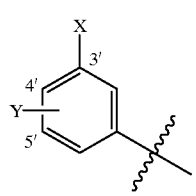

wherein:
Z is H;
X is halogen, CN, $C_1$ alkoxy, or $NO_2$;

Y is on the 4' or 5' position and is selected from the group consisting of H and F.
25. The compound according to claim 22 wherein $R^4$ is the moiety:

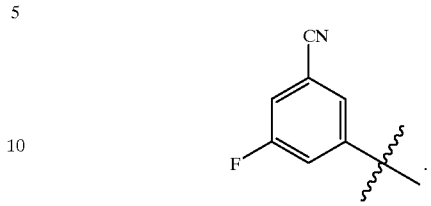

26. The compound according to claim 22 wherein:
$R^3$ is H, OH, $NH_2$, $C_1$ alkyl, substituted $C_1$ alkyl, or $COR^C$;
$R^C$ is H, $C_1$ to $C_3$ alkyl, or $C_1$ to $C_4$ alkoxy
$R^4$ is the five members ring b) of the structure:

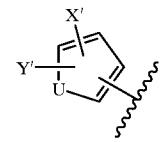

wherein:
U is O, S, or NH;
X' is halogen, CN, or $NO_2$;
Y' is H or $C_1$ to $C_4$ alkyl.
27. The compound according to claim 22 wherein $R^4$ is:

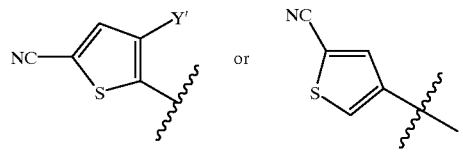

and Y' is H or $C_1$ to $C_4$ alkyl.
28. A pharmaceutical composition comprising a pharmaceutically effective amount of a compound according to claim 22 and a pharmaceutically effective carrier or excipient.
29. A method of inducing contraception in a mammal, the method comprising administering to a mammal in need thereof a pharmaceutically effective amount of a compound according to claim 22.
30. A method of treatment of benign or malignant neoplastic disease in a mammal, the method comprising administering to a mammal in need thereof a compound according to claim 22.
31. The method according to claim 30, wherein the benign or malignant neoplastic disease is selected from the group consisting of uterine myometrial fibroids, endometriosis, benign prostatic hypertrophy; carcinomas or adenocarcinomas of the endometrium, ovary, breast, colon, prostate, pituitary, meningioma and other hormone-dependent tumors.
32. A method of treatment in a mammal of carcinomas or adenocarcinomas of the endometrium, ovary, breast, colon, or prostate, the method comprising administering to a mammal in need thereof a compound according to claim 22.
33. The compound according to claim 22 which is 6-(3-Chloro-phenyl)-4,4-dimethyl-1,4-dihydro-3-oxa-1,8-diaza-naphthalene-2-one or a pharmaceutically acceptable salt thereof.

34. The compound according to claim 22, wherein $R^4$ is the substituted benzene ring a) having the substituents X, Y and Z as shown below:

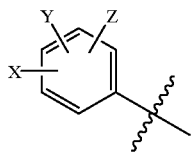

wherein X, Y, and Z are independent substituents selected from the group consisting of H, halogen, and CN.

35. The compound according to claim 22, wherein Q is O.

36. A compound having of the formula:

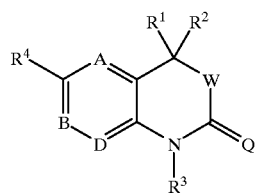

I wherein:
A, B and D are N or CH, with the proviso that one of A, B, and D is N;
Q is O, S, $NR^6$, or $CR^7R^8$;
$R^1 = R^2$ and are $CH_3$;
$R^3$ is H, OH, $NH_2$, $C_1$ to $C_6$ alkyl, substituted $C_1$ to $C_6$ alkyl, $C_3$ to $C_6$ alkenyl, substituted $C_3$ to $C_6$ alkenyl, or $COR^C$;
$R^C$ is H, $C_1$ to $C_3$ alkyl, substituted $C_1$ to $C_3$ alkyl, aryl, substituted aryl, $C_1$ to $C_4$ alkoxy, substituted $C_1$ to $C_4$ alkoxy, $C_1$ to $C_4$ aminoalkyl, or substituted $C_1$ to $C_4$ aminoalkyl;
$R^4$ is selected from the group consisting of a), b), and c):
a) a substituted benzene ring having the substituents X, Y and Z as shown below:

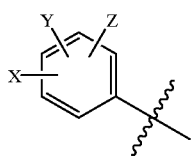

X is selected from the group consisting of halogen, CN, $C_1$ to $C_3$ alkyl, substituted $C_1$ to $C_3$ alkyl, $C_1$ to $C_4$ alkoxy, substituted $C_1$ to $C_4$ alkoxy, $C_1$ to $C_3$ thioalkoxy, substituted $C_1$ to $C_3$ thioalkoxy, amino, $C_1$ to $C_3$ aminoalkyl, substituted $C_1$ to $C_3$ aminoalkyl, $NO_2$, $C_1$ to $C_3$ perfluoroalkyl, 5 or 6 membered heterocyclic ring having in its backbone 1 to 3 heteroatoms, $COR^D$, $OCOR^D$, and $NR^ECOR^D$;
$R^D$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^E$ is H, $C_1$ to $C_3$ alkyl, or substituted $C_1$ to $C_3$ alkyl;
Y and Z are independent substituents selected from the group consisting of H, halogen, CN, $NO_2$, $C_1$ to $C_3$ alkoxy, $C_1$ to $C_4$ alkyl, and $C_1$ to $C_3$ thioalkoxy;

b) a five membered ring having in its backbone 1, 2, or 3 heteroatoms selected from the group consisting of O, S, SO, $SO_2$ and $NR^5$ and having one or two independent substituents selected from the group consisting of H, halogen, CN, $NO_2$, $C_1$ to $C_3$ alkyl, $C_1$ to $C_3$ alkoxy, $C_1$ to $C_3$ aminoalkyl, $COR^F$, and $NR^GCOR^F$; and c) a six membered ring having in its backbone 2 or 3 heteroatoms selected from the group consisting of O, S, SO, $SO_2$ and $NR^5$ and having one or two independent substituents selected from the group consisting of H, halogen, CN, $NO_2$, $C_1$ to $C_3$ alkyl, $C_1$ to $C_3$ alkoxy, $C_1$ to $C_3$ aminoalkyl, $COR^F$, and $NR^GCOR^F$;

$R^F$ is H, $C_1$ to $C_3$ alkyl, substituted $C_1$ to $C_3$ alkyl, aryl, substituted aryl, $C_1$ to $C_3$ alkoxy, substituted $C_1$ to $C_3$ alkoxy, $C_1$ to $C_3$ aminoalkyl, or substituted $C_1$ to $C_3$ aminoalkyl;
$R^G$ is H, $C_1$ to $C_3$ alkyl, or substituted $C_1$ to $C_3$ alkyl;
$R^5$ is H, $C_1$ to $C_3$ alkyl, or $C_1$ to $C_4$ $CO_2$ alkyl;
W is O;
or a pharmaceutically acceptable salt thereof.

37. A pharmaceutical composition comprising a pharmaceutically effective amount of a compound according to claim 36 and a pharmaceutically effective carrier or excipient.

38. A method of inducing contraception in a mammal, the method comprising administering to a mammal in need thereof a pharmaceutically effective amount of a compound according to claim 36.

39. A method of treatment of benign or malignant neoplastic disease in a mammal, the method comprising administering to a mammal in need thereof a compound according to claim 36.

40. The method according to claim 39 wherein the benign or malignant neoplastic disease is selected from the group consisting of uterine myometrial fibroids, endometriosis, benign prostatic hypertrophy; carcinomas or adenocarcinomas of the endometrium, ovary, breast, colon, prostate, pituitary, meningioma and other hormone-dependent tumors.

41. A method of treatment in a mammal of carcinomas or adenocarcinomas of the endometrium, ovary, breast, colon, or prostate, the method comprising administering to a mammal in need thereof a compound according to claim 36.

42. The compound according to claim 36 wherein:
$R^3$ is H, OH, $NH_2$, $C_1$ to $C_6$ alkyl, substituted $C_1$ to $C_6$ alkyl, or $COR^C$;
$R^C$ is H, $C_1$ to $C_4$ alkyl, or $C^1$ to $C_4$ alkoxy;
$R^4$ is selected from the group consisting of (i), (ii) and (iii):
(i) the substituted benzene ring a) of structure:

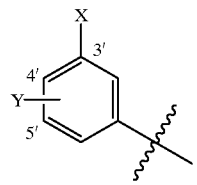

wherein:
Z is H;
X is selected from the group consisting of halogen, CN, $C_1$ to $C_3$ alkoxy, $C_1$ to $C_3$ alkyl, $NO_2$, $C_1$ to $C_3$ perfluoroalkyl, 5 membered heterocyclic ring having in its backbone 1 to 3 heteroatoms, and $C_1$ to $C_3$ thioalkoxy; and Y is on the 4' or 5' position and is selected from the group consisting of H, halogen, CN, $NO_2$, $C_1$ to $C_3$ alkoxy, $C_1$ to $C_4$ alkyl, and $C_1$ to $C_3$ thioalkoxy;

(ii) the five membered ring b) of the structure:

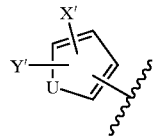

wherein:

U is O, S, or $NR^5$;

$R^5$ is H, $C_1$ to $C_3$ alkyl, or $C_1$ to $C_4$ $CO_2$ alkyl;

X' is selected from the group consisting of halogen, CN, $NO^2$, $C_1$ to $C_3$ alkyl, and $C_1$ to $C_3$ alkoxy;

Y' is selected from the group consisting of H and $C_1$ to $C_4$ alkyl;

(iii) the six membered ring c) of the structure:

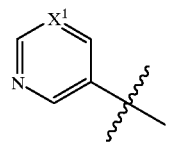

$X^1$ is N.

43. The compound according to claim 36 wherein:

$R^3$ is H, OH, $NH_2$, $C_1$ alkyl, substituted $C_1$ alkyl, or $COR_c$;

$R^c$ H, $C_1$ to $C_3$ alkyl, or $C_1$ to $C_4$ alkoxy;

$R^4$ is the substituted benzene ring a) of the structure as shown below:

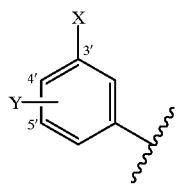

wherein:

Z is H;

X is halogen, CN, $C_1$ alkoxy, or $NO_2$;

Y is on the 40' or 5' position ans is selected from the group consisting of H and F.

44. The compound according to claim 36 wherein $R^4$ is moiety:

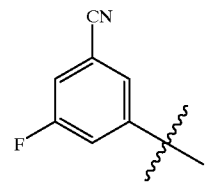

45. The compound according to claim 36 wherein:

$R^3$ is H, OH $NH_2$, $C_1$ alkyl, substituted $C_1$ alkyl, or $COR^C$;

$R^C$ is H, $C^1$ to $C_3$ alkyl, or $C_1$ to $C_4$ alkoxy;

$R^4$ is the five membered ring b) of the structure:

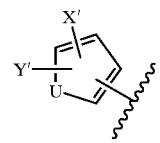

U is O, S, or NH;

X' is halogen, CN, or $NO_2$;

Y' is H or $C_1$ to $C_4$ alkyl.

46. The compound according to claim 36 wherein $R^4$ is:

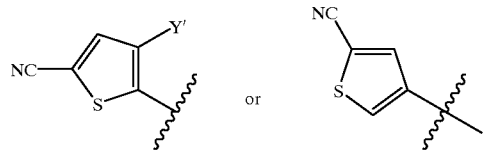

and Y' is H or $C_1$ to $C_4$ alkyl.

47. The compound according to claim 36 which is 6-(3-Chloro-phenyl)-4,4-dimethyl-1,4-dihydro-3-oxa-1,8-diaza-naphthalene-2-one.

48. The compound according to claim 36, wherein $R^4$ is the substituted benzene ring a) having the substituents X, Y and Z as shown below:

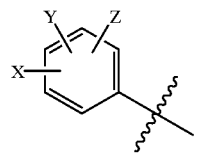

wherein X, Y, and Z are independent substituents selected from the group consisting of H, halogen, and CN.

49. The compound according to claim 36, wherein Q is O.

* * * * *

UNITED STATES PATENT AND TRADEMARK OFFICE
CERTIFICATE OF CORRECTION

PATENT NO. : 6,369,056 B1
DATED : April 9, 2002
INVENTOR(S) : Puwen Zhang et al.

It is certified that error appears in the above-identified patent and that said Letters Patent is hereby corrected as shown below:

Title page,
Item [57], ABSTRACT,
Line 17, replace "$NR_6$" with -- $NR^6$ --.

Column 6,
Line 53, replace "allyl, substituted $C_1$ to $C_3$ allyl, aryl," with -- alkyl, substituted $C_1$ to $C_3$ allyl, aryl, --.

Column 8,
Line 26, replace "allyl," with -- alkyl, --.

Column 9,
Line 6, replace "allyl," with -- alkyl, --.
Line 44, replace "$R_1$" with -- $R^1$ --.

Column 22,
Line 16, replace "fill" with -- full --.

Column 23,
Line 17, replace "fill" with -- full --.

Column 24,
Line 24, replace "fill" with -- full --.

Column 27,
Line 21, replace "Decidual response: $[(D-C)/C]x400\%$" with -- Decidual response: $[(D-C)/C]x100\%$ --.

Column 33,
Line 62, replace "$C_8$" with -- $C_3$ --.

Column 40,
Line 49, replace "$C^1$" with -- $C_1$ --.

UNITED STATES PATENT AND TRADEMARK OFFICE
CERTIFICATE OF CORRECTION

PATENT NO. : 6,369,056 B1
DATED : April 9, 2002
INVENTOR(S) : Puwen Zhang et al.

It is certified that error appears in the above-identified patent and that said Letters Patent is hereby corrected as shown below:

Column 41,
Line 20, replace "$NO^2$" with -- $NO_2$ --.
Line 36, replace "$COR_c$;" with -- $COR^c$; --.

Column 42,
Line 15, replace "$C^1$" with -- $C_1$ --.

Signed and Sealed this

Seventeenth Day of September, 2002

Attest:

JAMES E. ROGAN
Attesting Officer
Director of the United States Patent and Trademark Office